(12) United States Patent
Huang et al.

(10) Patent No.: US 8,980,259 B2
(45) Date of Patent: Mar. 17, 2015

(54) COMBINATION THERAPY

(71) Applicants: Xizhong Huang, Southborough, MA (US); Malte Peters, Basel (CH); Karl Maria Schumacher, Darmstadt (DE); Zhu Alexander Cao, Acton, MA (US); Jennifer Lorraine Gansert, Simi Valley, CA (US); David Dong Eun Chang, Calabasas, CA (US)

(72) Inventors: Xizhong Huang, Southborough, MA (US); Malte Peters, Basel (CH); Karl Maria Schumacher, Darmstadt (DE); Zhu Alexander Cao, Acton, MA (US); Jennifer Lorraine Gansert, Simi Valley, CA (US); David Dong Eun Chang, Calabasas, CA (US)

(73) Assignees: Novartis AG, Basel (CH); Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 13/799,076

(22) Filed: Mar. 13, 2013

(65) Prior Publication Data

US 2014/0023661 A1    Jan. 23, 2014

Related U.S. Application Data

(60) Provisional application No. 61/673,809, filed on Jul. 20, 2012, provisional application No. 61/759,490, filed on Feb. 1, 2013.

(51) Int. Cl.
| | |
|---|---|
| *A61K 31/4439* | (2006.01) |
| *A61K 39/395* | (2006.01) |
| *C07K 16/28* | (2006.01) |
| *A61K 39/00* | (2006.01) |

(52) U.S. Cl.
CPC ......... *A61K 31/4439* (2013.01); *A61K 39/3955* (2013.01); *C07K 16/2863* (2013.01); *A61K 2039/505* (2013.01); *C07K 2316/96* (2013.01); *C07K 2317/565* (2013.01)
USPC ..................................... 424/130.1; 424/172.1

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. .................... | 424/450 |
| 7,871,611 B2 | 1/2011 | Calzone et al. | |
| 8,227,462 B2 | 7/2012 | Fairhurst et al. | |
| 8,476,268 B2 | 7/2013 | Fairhurst et al. | |
| 2010/0209420 A1* | 8/2010 | Lamb et al. ................ | 424/133.1 |

FOREIGN PATENT DOCUMENTS

| | | | |
|---|---|---|---|
| WO | WO2006/069202 A2 | 6/2006 | |
| WO | WO2008/079849 A2 | 7/2008 | |
| WO | WO2012/016970 A1 | 2/2012 | |

OTHER PUBLICATIONS

Sporn et al, "Chemoprevention of Cancer," Carcinogenesis, vol. 21 (2000), 525-530.*
Auerbach et al (Cancer and Metastasis Reviews, 2000, 19: 167-172).*
Gura T (Science, 1997, 278(5340): 1041-1042, encloses 1-5).*
Jain RK (Scientific American, Jul. 1994,58-65).*
Bertrand, et al: Synergy between an IGF-1R antibody and Raf/MEK/ERK and PI3K/Akt/mTOR pathway inhibitors in suppressing IGF-1R-mediated growth in hematopoietic cells; Leukemia; 2006; vol. 20, No. 7, pp. 1254-1260.
Samuels, et al: Oncogenic PI3K and its role in cancer; Current Opinion in Oncology, Current Science Ltd., U.S., 2006, vol. 18, No. 1, pp. 77-82.
Verheijen, et al: Phosphatidylinositol 3-kinase (PI3K) inhibitors as anticancer drugs; Drugs of the Future; 2007, vol. 32, No. 6, pp. 537-547.
Wee, et al: Class IA phosphoinositide 3-kinase isoforms and human tumorigenesis: implications for cancer drug discovery and development; Current Opinion in Oncology, Current Science Ltd., U.S.; 2008, vol. 20, No. 1, pp. 77-82.
International Search Report and Written Opinion, PCT/US2013/051345, dated Oct. 8, 2013, 14 pages.

* cited by examiner

*Primary Examiner* — Brian J Gangle
*Assistant Examiner* — Andrea McCollum
(74) *Attorney, Agent, or Firm* — Lathrop & Gage LLP; Brian C. Trinque

(57) ABSTRACT

The present invention relates to a pharmaceutical combination comprising an alpha-isoform specific phosphatidylinositol 3-kinase inhibitor compound, such as (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or pharmaceutically acceptable salt thereof, and an insulin-like growth factor-1 receptor (IGF1R) inhibitor (e.g., the IGF1R inhibitor ANTIBODY A, or a variant or derivative thereof), a pharmaceutical composition comprising such combination, methods for treating cancer comprising administration of therapeutically effective amounts of such inhibitors to a subject in need thereof, and uses of such combination for the treatment of cancer.

16 Claims, 2 Drawing Sheets

SEQUENCE LISTING

```
<160> NUMBER OF SEQ ID NOS: 10

<210> SEQ ID NO 1
<211> LENGTH: 449
<212> TYPE: PRT
<213> ORGANISM: Artificial Sequence
<220> FEATURE:
<223> OTHER INFORMATION: Synthetic: antibody A heavy chain

<400> SEQUENCE: 1

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45
```

```
Ile Gly Glu Ile Tyr His Ser Gly Ser Thr Asn Tyr Asn Pro Ser Leu
    50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Trp Thr Gly Arg Thr Asp Ala Phe Asp Ile Trp Gly Gln Gly
            100                 105                 110
Thr Met Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

```
<210> SEQ ID NO 2
<211> LENGTH: 219
<212> TYPE: PRT
<213> ORGANISM: Artificial Sequence
<220> FEATURE:
<223> OTHER INFORMATION: Synthetic: antibody A light chain

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 119
<212> TYPE: PRT
<213> ORGANISM: Artificial Sequence
<220> FEATURE:
<223> OTHER INFORMATION: Synthetic peptide

<400> SEQUENCE: 3

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

Ala Arg Trp Thr Gly Arg Thr Asp Ala Phe Asp Ile Trp Gly Gln Gly
            100                 105                 110

Thr Met Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic peptide

<400> SEQUENCE: 4

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Ser Asn Trp Trp Ser
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Glu Ile Tyr His Ser Gly Ser Thr Asn Tyr Asn Pro Ser Leu Lys Ser
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Trp Thr Gly Arg Thr Asp Ala Phe Asp Ile
1               5                   10

<210> SEQ ID NO 8
<211> LENGTH: 16

```
<212> TYPE: PRT
<213> ORGANISM: Artificial Sequence
<220> FEATURE:
<223> OTHER INFORMATION: Synthetic peptide

<400> SEQUENCE: 8

Arg Ser Ser Gln Ser Leu Leu His Ser Asn Gly Tyr Asn Tyr Leu Asp
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Leu Gly Ser Asn Arg Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Met Gln Gly Thr His Trp Pro Leu Thr
1               5
```

COMBINATION THERAPY

RELATED APPLICATIONS

This application claims priority to U.S. Provisional Application Ser. No. 61/673,809, filed Jul. 20, 2012, and to U.S. Provisional Application Ser. No. 61/759,490, filed Feb. 1, 2013, which are both incorporated herein by reference in their entireties.

FIELD OF THE INVENTION

The present invention relates to a pharmaceutical combination comprising an alpha-isoform specific phosphatidylinositol 3-kinase (PI3K) inhibitor and an insulin-like growth factor-1 receptor (IGF1R) inhibitor, a pharmaceutical composition comprising such combination, methods for treating cancer comprising administration of a therapeutically effective amount of such combination to a subject in need thereof, and uses of such combination for the treatment of cancer. Preferably, the invention relates to a pharmaceutical combination comprising the alpha-isoform specific phosphatidylinositol 3-kinase (PI3K) inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or pharmaceutically acceptable salt thereof, and the IGF1R inhibitor ANTIBODY A.

BACKGROUND OF THE INVENTION

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate (PIP$_2$) and phosphoinositol-3,4,5-triphosphate (PIP$_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., Cell 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, *Nature* 335:85 (1988); Fantl et al., Cell 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., Cell 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. In a variety of tumors, the genes for the p110α isoform, PIK3CA, and for Akt are amplified and increased protein expression of their gene products has been demonstrated in several human cancers. Further, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304:554 (2004); Samuels et al., *Cancer Cell* 7:561-573 (2005)).

Further, insulin-like growth factor-1 receptor (IGF-1R), a transmembrane tyrosine kinase, is widely expressed on normal tissues. The receptor is activated by binding of the natural ligands IGF-1 and IGF-2 and leads to activation of the PI3K/AKT pathway. Upon binding of a growth factor to a receptor tyrosine kinase, PI3K binds to the intracellular domain of the receptor tyrosine kinase. This interaction between receptor tyrosine kinase and PI3K occurs either directly or via adaptor molecules such as insulin receptor substrate 1 (IRS-1) leading to the activation of the lipid kinase activity. Upon activation, PI3K generates PIP3, a lipid "second messenger", which in turn activates AKT (PKB), a serine/threonine kinase that is probably the best understood downstream effector of PI3K. The PI3K signaling is negatively regulated by action of dual specificity protein phosphatases/3-PI phosphatases, namely the tumor suppressor PTEN.

Activation of the PI3K/AKT pathway associated with increased IGF-1R signaling is known to occur in various cancer types, such as breast cancer, ovarian cancer, pancreatic carcinoma, colorectal cancer and melanoma. IGF-1R is often found to be overexpressed by cancer cell lines and human cancers, and many cancer cell lines are mitogenically responsive to physiological concentrations of IGFs. IGF-1R overexpression, however, in contrast to other receptor tyrosine kinase receptors, does not appear to be associated with gene amplification or gene mutation. IGF-1R is found to establish resistance to epidermal growth factor receptor (EGFR) inhibitors in EGFR amplified tumors by loss of insulin-growth factor binding protein expression.

Many cancers, particularly those carrying EGFR amplification, IGF1R overexpression, PIK3CA amplification, and/or PIK3CA mutation are amenable to treatment with epidermal growth factor receptor (EGFR) inhibitors, IGF1R inhibitors, aromatase inhibitors, and/or chemotherapy. However, in many cases the cancers acquire resistance to these chosen therapeutic and ultimately become refractory to treatment.

In spite of numerous treatment options for cancer patients, there remains a need for effective and safe therapeutic agents and a need for their preferential use in combination therapy. In particular, there is a need in the art for novel methods of treating cancers, particularly those carrying EGFR amplification, EGFR amplification and PI3K signaling, IGF1R overexpression, PIK3CA amplification, and/or PIK3CA mutation cancers, especially those cancers that have been resistant and/or refractive to current therapies.

SUMMARY OF THE INVENTION

The present invention relates to a pharmaceutical combination comprising an alpha-isoform specific phosphatidylinositol 3-kinase (PI3K) inhibitor and an insulin-like growth factor-1 receptor (IGF1R) inhibitor.

Preferably, the present invention relates to a pharmaceutical combination comprising: (a) the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and (b) the IGF1R inhibitor, ANTIBODY A, comprising the heavy chain amino acid sequence set forth in SEQ ID NO:1 and the light chain amino acid sequence set forth in SEQ ID NO:2, herein. COMPOUND A and ANTIBODY A can be in a single formulation or unit dosage form, or in separate formulations or unit dosage forms. In an embodiment, COMPOUND A is administered orally, and ANTIBODY A is administered intravenously.

In specific embodiments of the pharmaceutical combination, the alpha-isoform specific PI3K inhibitor is the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof.

In specific embodiments of the pharmaceutical combination, the IGF1R inhibitor is an IGF1R inhibitory antibody comprising a heavy chain and a light chain, wherein the heavy chain comprises a variable region comprising three complementarity determining regions (CDRs) comprising amino acid sequences selected from the group consisting of SEQ ID NOs: 5, 6, and 7, and wherein the light chain comprises a variable region comprising three CDRs comprising amino acid sequences selected from the group consisting of SEQ ID NOs: 8, 9, and 10.

In other specific embodiments of the pharmaceutical combination, the IGF1R inhibitor is an antibody comprising a heavy chain variable region comprising the amino acid sequence of SEQ ID NO: 3, and a light chain variable region comprising the amino acid sequence of SEQ ID NO: 4.

In additional specific embodiments of the pharmaceutical combination, the IGF1R inhibitor is an antibody comprising a heavy chain comprising the amino acid sequence of SEQ ID NO: 1, and a light chain comprising the amino acid sequence of SEQ ID NO: 2 (ANTIBODY A).

In one embodiment, the present invention comprises a pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof and the IGF1R inhibitor ANTIBODY A for use in the treatment of cancer in a subject in need thereof. The combination of the present invention can be used to treat subjects suffering from cancers having EGFR amplification, IGF1R overexpression, PIK3CA amplification, and/or PIK3CA mutation. COMPOUND A and ANTIBODY A can be in a single formulation or unit dosage form, or in separate formulations or unit dosage forms. In an embodiment, COMPOUND A is administered orally, and ANTIBODY A is administered intravenously.

In a further embodiment, the present invention comprises a pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof and the IGF1R inhibitor ANTIBODY A for use in the treatment of cancers that are resistant or refractive to currently-available therapies, e.g., EGFR amplified, IGF1R overexpressed, PIK3CA amplification, and/or PIK3CA mutation, cancers that are resistant or refractive to EGFR inhibitors or IGF1R inhibitors, in a subject in need thereof.

In a further embodiment, the present invention comprises the combination of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof and ANTIBODY A displaying a synergistic effect.

The present invention provides a method of treating cancer in a subject (e.g., patient) by administering to the subject in need of such treatment a therapeutically effective amount or dose of a combination of an alpha-isoform specific PI3K inhibitor, such as COMPOUND A or a pharmaceutically acceptable salt thereof, and an IGF1R inhibitor, such as ANTIBODY A. COMPOUND A and ANTIBODY A can be in a single formulation or unit dosage form, or in separate formulations or unit dosage forms. In an embodiment, COMPOUND A is administered orally, and ANTIBODY A is administered intravenously.

In one embodiment, the present invention provides a method of treating cancer by administering to subject in need of such treatment a quantity of COMPOUND A or pharmaceutically acceptable salt thereof and ANTIBODY A which is jointly therapeutically effective for said treatment.

In a further embodiment, COMPOUND A and ANTIBODY A are in a single formulation or unit dosage form. In a further embodiment, COMPOUND A and ANTIBODY A are in separate formulations or unit dosage forms.

In a further embodiment, COMPOUND A and/or ANTIBODY A are administered at substantially the same time. In a further embodiment, COMPOUND A and/or ANTIBODY A are administered at different times. In a further embodiment, COMPOUND A is administered to the subject prior to administration of ANTIBODY A. In a further embodiment, ANTIBODY A is administered to the subject prior to administration of COMPOUND A.

In a further embodiment, COMPOUND A is administered at a dosage range from about 0.05 to about 50 mg, e.g., from 0.05 to 50 mg, per kilogram body weight of the recipient per day. In a further embodiment, ANTIBODY A is administered at a dosage of between about 9 and 20 mg/kg, e.g., between 9 and 20 mg/kg.

The present invention provides a method for treating a cancer that is resistant or refractive to prior treatment with an EGFR modulator or IGF1R inhibitor comprising administering a therapeutically effective amount of COMPOUND A or a pharmaceutically acceptable salt thereof and ANTIBODY A to a subject in need thereof.

The present invention further provides a method for the treatment of cancer that is resistant or refractive to treatment with the IGF1R inhibitor ANTIBODY A by administering a therapeutically effective amount of COMPOUND A or a pharmaceutically acceptable salt thereof.

The present invention provides a use of the pharmaceutical combination comprising COMPOUND A or a pharmaceutically acceptable salt thereof and ANTIBODY A for the manufacture of a pharmaceutical preparation or medicament for the treatment of cancer.

The present invention further provides the use of a pharmaceutical combination comprising COMPOUND A or a pharmaceutically acceptable salt thereof and ANTIBODY A for the manufacture of a pharmaceutical preparation or medicament for the treatment of cancer that is resistant or refractive to treatment with an EGFR modulator or IGF1R inhibitor.

The present invention further provides the use of COMPOUND A or a pharmaceutically acceptable salt thereof for the treatment of cancer that is resistant or refractive to treatment with the IGF1R inhibitor ANTIBODY A.

In one embodiment, the present invention relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers.

In a further embodiment, the present invention further relates to a pharmaceutical composition or pharmaceutical formulation comprising (a) COMPOUND A or a pharmaceutically acceptable salt thereof, and (b) ANTIBODY A, and optionally one or more pharmaceutically acceptable carriers, for use in the treatment of cancer.

In a further embodiment, the present invention relates to a combination therapy comprising (a) a pharmaceutical combination comprising COMPOUND A or a pharmaceutically acceptable salt thereof, and (b) a pharmaceutical composition comprising ANTIBODY A administered in separate pharmaceutical compositions to a subject in need thereof. COMPOUND A and ANTIBODY A can be in a single formulation or unit dosage form, or in separate formulations or unit dosage forms. In an embodiment, COMPOUND A is administered orally, and ANTIBODY A is administered intravenously.

DETAILED DESCRIPTION OF THE INVENTION

Figure 1:
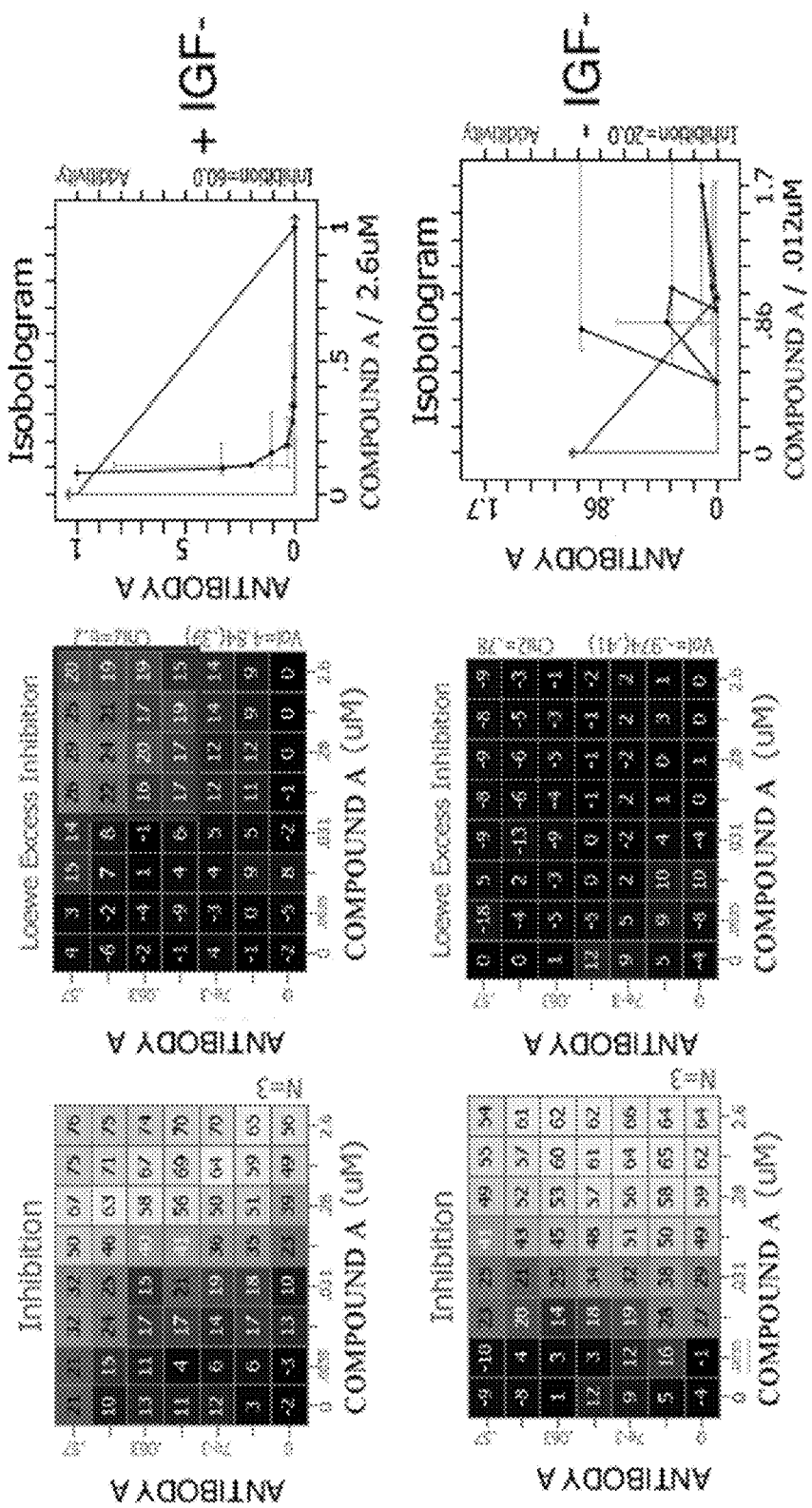
FIG. 1 is a series of graphs showing the effect of the combination of COMPOUND A with ANTIBODY A on MCF7 cell proliferation under the presence of IGF-1 (100 ng/ml). Briefly, MCF7 cells were treated in 384-well format for 5 days with COMPOUND A and ANTIBODY A in the presence of 100 ng/ml of IGF1 in SD medium. Cell viability was measured using the CELLTITER-GLO assay and % inhibition data was displayed numerically as 7×8 dose grid. Each data point represents averaged data from 3 wells+standard deviation, and the color spectrum also represents the level of the inhibition. A red rectangle highlights the region where the combination is more efficacious than the single agents the same dose.

The present invention relates to a pharmaceutical combination comprising an alpha-isoform specific phosphatidylinositol 3-kinase (PI3K) inhibitor and an insulin-like growth factor-1 receptor (IGF1R) inhibitor. Preferably, the present invention relates to a pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof, and the IGF1R inhibitor ANTIBODY A.

Certain terms used herein are described below. Compounds and antibodies of the present invention are described using standard nomenclature. Unless defined otherwise, all technical and scientific terms used herein have the same meaning as is commonly understood by one of skill in the art to which this invention belongs.

The term "pharmaceutical combination" as used herein refers to either a fixed combination in one dosage unit form, or non-fixed combination or a kit of parts for the combined administration where two or more therapeutic agents can be administered independently, at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The terms "alpha-isoform specific phosphatidylinositol 3-kinase inhibitor", "alpha-isoform specific PI3K inhibitor", "alpha-isoform selective phosphatidylinositol 3-kinase inhibitor", and "alpha-isoform selective PI3K inhibitor" as used herein refer to a compound that selectively targets, decreases or inhibits at least one activity of the alpha-isoform of PI3K with respect to beta and/or delta and/or gamma subtypes. Exemplary alpha-isoform specific PI3K inhibitors are disclosed in International PCT Application WO2010/029082, which is hereby incorporated by reference in its entirety.

The term "IGF1R inhibitor" as used herein refers to an antibody or a compound that targets, decreases, or inhibits at least one activity of an Insulin Growth Factor-1 Receptor. Exemplary IGF1R inhibitors are disclosed in U.S. Pat. No. 7,871,611, which is hereby incorporated by reference in its entirety.

The term "pharmaceutically acceptable" as used herein refers to those compounds, antibodies, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination", "fixed dose" and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination" or "kit of parts" means that the active ingredients, e.g. COMPOUND A and ANTIBODY A, are both administered to a patient as separate entities either simultaneously, concurrently or sequentially with no specific time limits, wherein such administration provides therapeutically effective levels of the two compounds in the body of the warm-blooded animal in need thereof. The latter also applies to cocktail therapy, e.g., the administration of three or more active ingredients.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, injections, infusions, patches, or the like, administered to the patient at the same time.

An "oral dosage form" includes a unit dosage form prescribed or intended for oral administration.

The term "treat" is used herein to mean to relieve, reduce, prevent, eliminate, or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

The term "effective amount" or "therapeutically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "subject" is intended to include animals. Examples of subjects include mammals, e.g., humans, apes, monkeys, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value.

The present invention relates to a pharmaceutical combination comprising an alpha-isoform specific phosphatidylinositol 3-kinase (PI3K) inhibitor and an insulin-like growth factor-1 receptor (IGF1R) inhibitor.

In certain embodiments, the pharmaceutical combination of the present invention comprises an alpha-isoform specific PI3K inhibitor compound with the following chemical formula (A):

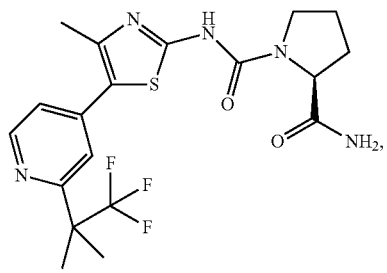

(A)

or pharmaceutically acceptable salts thereof. The compound of formula (A) is also known as the chemical compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (hereinafter referred to as "COMPOUND A"). COMPOUND A is described in PCT Application No. WO2010/029082, which is hereby incorporated by reference in its entirety, and methods for its preparation have been described, for example, in Example 15 therein.

As used herein, "salts" (which, what is meant by "or salts thereof" or "or a salt thereof"), can be present alone or in mixture with free compound of the formula (A) and are preferably pharmaceutically acceptable salts. Such salts are formed, for example, as acid addition salts, preferably with organic or inorganic acids, from compounds of formula (A) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of compounds of formula (A) are preferably pharmaceutically acceptable salts; suitable counter-ions forming pharmaceutically acceptable salts are known in the field.

As used herein, the term "pharmaceutically acceptable salts" refers to the salts of COMPOUND A. These salts can be prepared in situ during the final isolation and purification of the compound, or by separately reacting the base or acid functions with a suitable organic or inorganic acid or base, respectively.

Unless otherwise specified, or clearly indicated by the text, reference to compounds useful in the combination therapy of the invention includes both the free base of COMPOUND A, and all pharmaceutically acceptable salts of COMPOUND A.

In certain embodiments, the pharmaceutical combination of the present invention comprises the IGF1R inhibitory antibody, ANTIBODY A, disclosed in U.S. Pat. No. 7,871,611, which is incorporated herein by reference in its entirety. Specifically, ANTIBODY A comprises the heavy chain amino acid sequence set forth in SEQ ID NO:1 and the light chain amino acid sequence set forth in SEQ ID NO:2, herein.

```
ANTIBODY A heavy chain
                                                         (SEQ ID NO: 1)
QVQLQESGPGLVKPSGTLSLTCAVSGGSISSSNWWSWVRQPPGKGLEWIGEIYHSGSTNYNPSL

KSRVTISVDKSKNQFSLKLSSVTAADTAVYYCARWTGRTDAFDIWGQGTMVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

ANTIBODY A light chain
                                                         (SEQ ID NO: 2)
DVVMTQSPLSLPVTPGEPASISCRSSQSLLHSNGYNYLDWYLQKPGQSPQLLIYLGSNRASGVP

DRFSGSGSGTDFTLKISRVEAEDVGVYYCMQGTHWPLTFGQGTKVEIKRTVAAPSVFIFPPSDE

QLKSGTASVVCLLNNFYPREAKVQWKVDNALQSGNSQESVTEQDSKDSTYSLSSTLTLSKADYE

KHKVYACEVTHQGLSSPVTKSFNRGEC
```

Antibody variable region and CDR amino acid sequences of ANTIBODY A are set forth below:

```
Heavy chain variable region
                                                         (SEQ ID NO: 3)
QVQLQESGPGLVKPSGTLSLTCAVSGGSISSSNWWSWVRQPPGKGLEWIGEIYHSGSTNYNPSL

KSRVTISVDKSKNQFSLKLSSVTAADTAVYYCARWTGRTDAFDIWGQGTMVTVSS

Light chain variable region
                                                         (SEQ ID NO: 4)
DVVMTQSPLSLPVTPGEPASISCRSSQSLLHSNGYNYLDWYLQKPGQSPQLLIYLGSNRASGVP

DRFSGSGSGTDFTLKISRVEAEDVGVYYCMQGTHWPLTFGQGTKVEIK

Heavy chain CDR1
                                                         (SEQ ID NO: 5)
SSNWWS Heavy chain CDR2
                                                         (SEQ ID NO: 6)
EIYHSGSTNYNPSLKS Heavy chain CDR3
                                                         (SEQ ID NO: 7)
WTGRTDAFDI Light chain CDR1
                                                         (SEQ ID NO: 8)
RSSQSLLHSNGYNYLD Light chain CDR2
                                                         (SEQ ID NO: 9)
LGSNRAS Light chain CDR3
                                                         (SEQ ID NO: 10)
MQGTHWPLT
```

Variants of ANTIBODY A can also be used in the combination therapy and methods disclosed herein. In one embodiment, the variant is an antibody comprising the heavy chain variable region amino acid sequence set forth in SEQ ID NO: 3. In another embodiment, the variant is an antibody comprising the light chain variable region amino acid sequence set forth in SEQ ID NO: 4. In another embodiment, the variant is an antibody comprising the heavy chain and light chain variable region amino acid sequences set forth in SEQ ID NO: 3 and SEQ ID NO: 4, respectively. In another embodiment, the variant is an antibody comprising the heavy chain CDR1, 2 and 3 amino acid sequences set forth in SEQ ID NO: 5, 6, and 7, respectively. In another embodiment, the variant is an antibody comprising the light chain CDR1, 2 and 3 amino acid sequences set forth in SEQ ID NO: 8, 9, and 10, respectively. In a further embodiment, the variant is an antibody comprising the heavy chain CDR1, 2 and 3 amino acid sequences set forth in SEQ ID NO: 5, 6, and 7, respectively, and the light chain CDR1, 2 and 3 amino acid sequences set forth in SEQ ID NO: 8, 9, and 10, respectively.

Further variants of ANTIBODY A, its variable domains, constant regions, CDRs, and post-translational modifications, and additional anti-IGF1R antibodies and variants thereof, suitable for use in the combinations of the present invention, are provided in U.S. Pat. No. 7,871,611, which is incorporated herein by reference in its entirety. In one particular embodiment, the variant of ANTIBODY A comprises a light chain variable region that is at least 90% identical to SEQ ID NO: 4. In another particular embodiment, the variant of ANTIBODY A comprises a heavy chain variable region that is at least 90% identical to SEQ ID NO: 3. In another particular embodiment, the variant of ANTIBODY A comprises a light chain variable region that is at least 90% identical to SEQ ID NO: 4 and a heavy chain variable region that is at least 90% identical to SEQ ID NO: 3.

In other embodiments, a different IGF1R inhibitor is used. Such inhibitors include, but are not limited to, antibodies (including fragments and derivatives thereof), peptibodies, and AVIMERS™ (Amgen, Inc., Thousand Oaks, Calif.) that bind to IGF1R, IGF-1, or IGF-2, soluble derivatives of IGF-1R, small molecules that bind to IGF-1R, IGF-1, IGF-2, IRS1, SHC, GRB2, SOS1, SHP2, or any other molecule that acts in the IGF-1R signaling cascade, IGF-1 or IGF-2 binding proteins (and derivatives thereof), inhibitory nucleic acids (such as siRNA) and derivatives thereof (including peptide nucleic acids). Non-limiting examples of such molecules can be found in, for example, U.S. Pat. No. 7,329,7347 (published Feb. 12, 2008), U.S. Pat. No. 173,005 (issued Feb. 6, 2007), U.S. Pat. No. 7,071,300 (issued Jul. 4, 2006), U.S. Pat. No. 7,020,563 (issued Mar. 28, 2006), U.S. Pat. No. 6,875,741 (issued Apr. 5, 2005); U.S. Pat. App. Pub. No. 07/0299010 (published Dec. 27, 2007), 07/0265189 (published Nov. 15, 2007), 07/0135340 (published Jun. 14, 2007), 07/0129399 (published Jun. 7, 2007), 07/0004634 A1 (published Jan. 4, 2007), 05/0282761 A1 (published Dec. 22, 2005), 05/0054638 A1 (published Mar. 10, 2005), 04/0023887 A1 (published Feb. 5, 2004), 03/0236190 A1 (published Dec. 25, 2003), 03/0195147 A1 (published Oct. 16, 2003); PCT Pub. No. WO 07/099171 (published Sep. 7, 2007), WO 07/099166 (published Sep. 7, 2007), 07/031745 (published Mar. 22, 2007), WO 07/029106 (published Mar. 15, 2007), WO 07/029107 (published Mar. 15, 2007), WO 07/004060 (published Jan. 11, 2007), WO 06/074057 A2 (published Jul. 13, 2006), WO 06/069202 A2 (published Jun. 29, 2006), WO 06/017443 A2 (published Feb. 16, 2006), WO 06/012422 A1 (published Feb. 2, 2006), WO 06/009962 A2 (published Jan. 26, 2006), WO 06/009950 A2 (published Jan. 26, 2006), WO 06/009947 A2 (published Jan. 26, 2006), WO 06/009933 A2 (published Jan. 26, 2006), WO 05/097800 A1 (Oct. 20, 2005), WO 05/082415 A2 (published Sep. 9, 2005), WO 05/037836 A2 (published Apr. 28, 2005), WO 03/070911 A2 (published Aug. 28, 2003), WO 99/28347 A2 (published Jun. 10, 1999); European Pat. No. EP 1 732 898 B1 (published Jan. 23, 2008), EP 0 737 248 B1 (published Nov. 14, 2007), European Pat. App. No. EP 1 496 935 A2 (published Jan. 19, 2005) and EP 1 432 433 A2 (published Jun. 30, 2004), and D'ambrosio et al., 1996, Cancer Res. 56:4013-20, each of which is incorporated herein by reference in its entirety. Specific examples of such molecules include OSI-906 (OSI Pharmaceuticals, Melvilee, N.Y.), BMS 536924 (Wittman et al., 2005, J Med. Chem. 48:5639-43; Bristol Myers Squibb, New York, N.Y.), XL228 (Exelexis, South San Francisco, Calif.), INSM-18, NDGA, and rhIGFBP-3 (Insmed, Inc., Richmond, Va.; Breuhahn et al, 2002006, Curr Cancer Ther Rev. 2:157-67; Youngren et al., 2005, Breast Cancer Res Treatment 94:37-46; U.S. Pat. No. 6,608,108), each of which reference is incorporated herein by reference in its entirety.

In one aspect, any suitable anti-IGF1R antibody, antibody fragment, or antibody derivative can be used in the combinations and methods of the present invention. In one embodiment, the antibody, antibody fragment, or antibody derivative binds to the extracellular domain of IGF1R. In another embodiment, the antibody, antibody fragment, or antibody derivative competes for binding to IGF1R with IGF-1 and/or IGF-2. In another embodiment, the antibody, antibody fragment, or antibody derivative, when bound to IGF1R, reduces the amount of IGF-1 and/or IGF-2 that binds to the IGF1R. In another embodiment, the antibody, antibody fragment, or antibody derivative binds to the L1 subdomain of the IGF1R extracellular domain. In another embodiment, the antibody, antibody fragment, or antibody derivative binds to the CR subdomain of the IGF1R extracellular domain. In another embodiment, the antibody, antibody fragment, or antibody derivative binds to the L2 subdomain of the IGF1R extracellular domain. In another embodiment, the antibody, antibody fragment, or antibody derivative binds to the FnIII1 subdomain of the IGF1R extracellular domain. In another embodiment, the antibody, antibody fragment, or antibody derivative binds to the FnIII2-ID subdomain of the IGF1R extracellular domain. In another embodiment, the antibody, antibody fragment, or antibody derivative binds to the FnIII subdomain of the IGF1R extracellular domain. In another embodiment, the antibody, antibody fragment, or antibody derivative binds to more than one IGF1R extracellular domain. Non-limiting examples of anti-IGF1R antibodies that can be used in the methods of the present invention include each of the antibodies identified in U.S. Pat. No. 7,871,611, incorporated herein by reference in its entirety, as L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20, H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, and IGF1R-binding fragments and derivatives thereof. Other non-limiting examples of anti-IGF1R antibodies for use in the methods of the present invention include those described in U.S. Pat. App. Pub. No. 06/0040358 (published Feb. 23, 2006), 05/0008642 (published Jan. 13, 2005), 04/0228859 (published Nov. 18, 2004), e.g., antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; PCT Pub. No. WO 06/138729 (published Dec. 28, 2006), WO 05/016970 (published Feb. 24, 2005), and Lu et al., 2004, J Biol. Chem. 279:2856-65, e.g., antibodies 2F8, A12, and IMCA12 as described therein; PCT Pub. No. WO 07/012614 (published Feb. 1, 2007), WO 07/000328 (published Jan. 4, 2007), WO 06/013472 (published Feb. 9, 2006), Ser. No. 05/058,967 (published Jun. 30, 2005), Ser. No. 03/059,951 (published Jul. 24, 2003), U.S. Pat. App. Pub. No. 05/0084906 (published Apr. 21, 2005), e.g., antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; U.S. Pat. App. Pub. No. 05/0249728 (published Nov. 10, 2005), 05/0186203 (published Aug. 25, 2005), 04/0265307 (published Dec. 30, 2004), 03/0235582 (published Dec. 25, 2003), Maloney et al., 2003, Cancer Res. 63:5073-83, e.g., antibody EM164, resurfaced EM164, humanized EM164, huEM164 v1.0, huEM164 v1.1, huEM164 v1.2, and huEM164 v1.3, as described therein; U.S. Pat. No. 7,037,498 (issued May 2, 2006), U.S. Pat. App.

No. 05/0244408 (published Nov. 30, 2005), 04/0086503 (published May 6, 2004), Cohen, et al., 2005, Clinical Cancer Res. 11:2063-73, e.g., antibody CP-751,871, each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; U.S. Pat. App. No. 05/0136063 (published Jun. 23, 2005), 04/0018191 (published Jan. 29, 2004), e.g. antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; U.S. Pat. App. No. 04/0202655 (published Oct. 14, 2004), e.g., antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; U.S. patent application Ser. No. 07/024,3194 (published Oct. 18, 2007), e.g., antibodies M13-C06, M14-G11, M14-C03, M14-B01, M12-E01, and M12-G04, and antibodies produced by hybridomas P2A7.3E11, 2008.3B8, P1A2.2B11, 20D8.24B11, P1E2.3B12, and P1G10.2B8.

Each of the foregoing references is incorporated herein by reference in its entirety. Also suitable for use are antibodies, antibody fragments, or antibody derivatives that compete for binding to IGF1R with one of the aforementioned antibodies. In one embodiment, the antibody, antibody fragment, or antibody derivative binds to the same epitope as one of the aforementioned antibodies, or to an epitope that overlaps with the epitope of one of the aforementioned antibodies.

As used herein, a "combination of agents", "combination of the invention" and similar terms refer to a combination of two types of agents: (1) an alpha-isoform selective PI3K inhibitor, such as the alpha-isoform selective PI3K inhibitor COMPOUND A or pharmaceutically acceptable salts thereof and (2) an IGF1R inhibitor, such as the IGF1R inhibitor ANTIBODY A or a variant or derivative thereof. The alpha-isoform selective PI3K inhibitor and the IGF1R inhibitor can be in a single formulation or unit dosage form, or in separate formulations or unit dosage forms. In an embodiment, the alpha-isoform selective PI3K inhibitor is administered orally, and the IGF1R inhibitor is administered intravenously.

Provided herein is a combination therapy comprising an alpha-isoform selective PI3K inhibitor (for example, COMPOUND A) and an IGF1R inhibitor (for example, ANTIBODY A). Administration of the combination includes administration of the combination in a single formulation or unit dosage form, administration of the individual agents of the combination concurrently but separately, or administration of the individual agents of the combination sequentially by any suitable route. The dosage of the individual agents of the combination can require more frequent administration of one of the agent(s) as compared to the other agent(s) in the combination. Therefore, to permit appropriate dosing, packaged pharmaceutical products can contain one or more dosage forms that contain the combination of agents, and one or more dosage forms that contain one of the combination of agents, but not the other agent(s) of the combination.

In one embodiment, the present invention comprises a pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof and the IGF1R inhibitor ANTIBODY A for use in the treatment of cancer in a subject in need thereof. The combination of the present invention can be used to treat subjects suffering from cancers having, for example, EGFR amplification, IGF1R overexpression, PIK3CA amplification, and/or PIK3CA mutation.

In a further embodiment, the present invention comprises a pharmaceutical combination comprising the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof and the IGF1R inhibitor ANTIBODY A for use in the treatment of cancers that are resistant or refractive to currently-available therapies, e.g., EGFR amplification, IGF1R overexpression, PIK3CA amplification, and/or PIK3CA mutation cancers that are resistant or refractive to EGFR inhibitors or IGF1R inhibitors, in a subject in need thereof.

In one embodiment, the combination displays a synergistic effect. The term "synergistic effect" as used herein, refers to action of two agents such as, for example, COMPOUND A or a pharmaceutically acceptable salt thereof, and ANTIBODY A, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Methods of Treatment Using an Alpha-Isoform Specific Phosphatidylinositol 3-Kinase Inhibitor And an IGF1R Inhibitor Combination The present invention provides a method of treating cancer in a subject in need thereof by administering a combination of the invention to the subject in need thereof.

In one embodiment, the present invention provides a method of treating cancer in a subject (e.g., patient) by administering to the subject in need of such treatment a therapeutically effective amount or dose of a combination of COMPOUND A, or a pharmaceutically acceptable salt thereof, and ANTIBODY A, or a variant or derivative thereof. COMPOUND A and ANTIBODY A can be in a single formulation or unit dosage form, or in separate formulations or unit dosage forms. In an embodiment, COMPOUND A is administered orally, and ANTIBODY A is administered intravenously.

In a further embodiment, the present invention provides a method of treating cancer by administering to a subject in need of such treatment a quantity of COMPOUND A, or a pharmaceutically acceptable salt thereof, and a quantity of ANTIBODY A, or a variant or derivative thereof, which, jointly, is therapeutically effective for said treatment.

Examples of types of cancer which can be treated with the combination of the present invention include, without limitation, sarcoma, lung (e.g, non-small cell lung cancer and small cell lung cancer), bronchus, prostate, breast (including sporadic breast cancers, PI3KCA mutant breast cancers, luminal breast cancers and sufferers of Cowden disease), pancreas (including, for example, metastatic pancreatic cancer and locally advanced pancreatic cancer), gastrointestinal cancer, colon, rectum, colon carcinoma, colorectal adenoma, thyroid, liver, intrahepatic bile duct, hepatocellular, adrenal gland, stomach, gastric, glioma (e.g., adult, childhood brain stem, childhood cerebral astrocytoma, childhood visual pathway and hypothalamic), glioblastoma, endometrial, melanoma, kidney, renal pelvis, urinary bladder, uterine corpus, uterine cervix, vagina, ovary, multiple myeloma, esophagus, a leukaemia (e.g., acute lymphoblastic, acute myeloid, chronic lymphocytic, chronic myelogenous, and hairy cell), acute myelogenous leukemia, chronic myelogenous leukemia, lymphocytic leukemia, myeloid leukemia, brain (e.g., brain stem glioma, cerebellar astrocytoma, cerebral astrocytoma/malignant glioma, ependymoma, medulloblastoma, supratentorial primitive neuroectodermal tumors, visual pathway and hypothalamic glioma), lip and oral cavity and pharynx, larynx, small intestine, melanoma, villous colon adenoma, a neoplasia, a neoplasia of epithelial character, lymphomas (e.g., AIDS-related, Burkitt's, Cutaneous T-Cell, Non-Hodgkin's, and primary central nervous system), a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, and Walden stroem disease.

Further examples of types of cancer which can be treated with the combination of the present invention include, without limitation, adrenocortical carcinoma, AIDS-related cancers, Childhood Cerebellar Astrocytoma, Childhood Cerebral Astrocytoma, Basal Cell Carcinoma, extrahepatic bile duct cancer, osteosarcoma/malignant fibrous histiocytoma bone cancer, bronchial adenomas/carcinoids, carcinoid tumor, gastrointestinal carcinoid tumor, primary central nervous system, cerebellar astrocytoma, childhood cancers, Chronic Lymphocytic Leukemia, Chronic Myelogenous Leukemia, Chronic Myeloproliferative Disorders, ependymoma, Ewing's Family of Tumors, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors (e.g., extracranial, extragonadal, and ovarian), gestational trophoblastic tumor, hairy cell leukemia, hepatocellular cancer, hypopharyngeal cancer, hypothalamic and visual pathway glioma, islet cell carcinoma (endocrine pancreas), Kaposi's Sarcoma, laryngeal cancer, malignant fibrous histiocytoma of bone/osteosarcoma, medulloblastoma, merkel cell carcinoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, myelogenous leukemia, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, islet cell pancreatic cancer, parathyroid cancer, pheochromocytoma, pineoblastoma, pituitary tumor, pleuropulmonary blastoma, ureter transitional cell cancer, retinoblastoma, rhabdomyo sarcoma, salivary gland cancer, Sezary Syndrome, non-melanoma skin cancer, Merkel Cell Skin Carcinoma, squamous cell carcinoma, testicular cancer, thymoma, gestational trophoblastic tumor, and Wilms' Tumor.

In certain specific embodiments, the cancer that is treated with the combination of the present invention is, breast cancer, colorectal cancer, pancreatic cancer, ovarian cancer or melanoma.

In certain embodiments, the cancer is an EGFR amplified, IGF1R overexpressing, PIK3CA amplified, and/or PIK3CA mutated cancer. Suitable EGFR amplified, IGF1R overexpressing, PIK3CA amplified, and/or PIK3CA mutated cancers include, without limitation, some breast cancers, colorectal cancers, pancreatic cancers, ovarian cancers, and melanomas.

In certain embodiments, the cancer is a solid tumor. In other embodiments, the cancer is an EGFR amplified, IGF1R overexpressing, PIK3CA amplified, and/or PIK3CA mutated solid tumor.

In further embodiments, the cancer is PIK3CA mutated or amplified breast cancer, particularly hormone receptor positive breast cancer.

In other embodiments, the cancer is PIK3CA mutated or amplified ovarian cancer.

The cancer to be treated can be a EGFR-amplified cancer. The term "EGFR-amplified cancer" refers to a cancer in which the cancer cells comprise an amplification of the tyrosine kinase domain of epidermal growth factor receptor (EGFR), e.g., EGFR1, EGFR2, or EGFR3.

The term "EGFR inhibitor" refers to a compound that inhibits, decreases, lowers, or reduces at least one activity of an epidermal growth factor receptor (EGFR). Examples of EGFR inhibitors include, but are not limited to, [6,7-bis(2-methoxyethoxy)-4-quinazolin-4-yl]-(3-ethynylphenyl) amine (also known as OSI-774), erlotinib, CI-1033 (formerly known as PD183805), AG-1478, CGP-59326, PKI-166, EKB-569, lapatinib or lapatinib ditosylate; and gefitinib, AG490 (a tyrphostin), ARRY-334543, BIBW-2992, EKB-569, ZD6474, BMS-599626 (Bristol-Myers Squibb), cetuximab, panitumumab, and MDX-447.

The structure of the active agents identified by code nos., generic or trade names can be taken from the actual edition of the standard compendium "The Merck Index" or from databases, e.g., Patents International (e.g., IMS World Publications). The corresponding content thereof is incorporated by reference.

In one embodiment, the present invention provides a method of treating cancer by administering to subject in need of such treatment a quantity of COMPOUND A, or pharmaceutically acceptable salt thereof, and ANTIBODY A, or a variant or derivative thereof, which, jointly, are therapeutically effective for said treatment.

In a further embodiment, COMPOUND A and ANTIBODY A, or a variant or derivative thereof, are in a single formulation or unit dosage form. In a further embodiment, COMPOUND A and ANTIBODY A, or a variant or derivative thereof, are in separate formulations or unit dosage forms.

In a further embodiment, COMPOUND A and/or ANTIBODY A, or a variant or derivative thereof, are administered at substantially the same time.

In a further embodiment, COMPOUND A and/or ANTIBODY A, or a variant or derivative thereof, are administered at different times. In a further embodiment, COMPOUND A is administered to the subject prior to administration of ANTIBODY A, or a variant or derivative thereof. In a further embodiment, ANTIBODY A, or a variant or derivative thereof, is administered to the subject prior to administration of COMPOUND A. In an embodiment, COMPOUND A is administered orally, and ANTIBODY A is administered intravenously.

The present invention further provides a method for treating a cancer that is resistant or refractive to treatment with an EGFR modulator or IGF1R inhibitor comprising administering a therapeutically effective amount of COMPOUND A or a pharmaceutically acceptable salt thereof to a subject in need thereof.

In one embodiment, the present invention provides a method for treating a cancer that is resistant or refractive to treatment with the IGF1R inhibitor ANTIBODY A, or a variant or derivative thereof, comprising administering a therapeutically effective amount of COMPOUND A or a pharmaceutically acceptable salt thereof to a subject in need thereof.

The present invention further provides a method for the treatment of cancer that is resistant or refractive to treatment with the IGF1R inhibitor ANTIBODY A, or a variant or derivative thereof, by administering a therapeutically effective amount of COMPOUND A or a pharmaceutically acceptable salt thereof.

The present invention further provides a use of the pharmaceutical combination comprising COMPOUND A, or a pharmaceutically acceptable salt thereof, and ANTIBODY A, or a variant or derivative thereof, for the manufacture of a pharmaceutical preparation or medicament for the treatment of cancer. In one embodiment, the cancer to be treated is a cancer identified above, which is hereby incorporated by reference in its entirety.

The present invention further provides the use of a pharmaceutical combination comprising COMPOUND A, or a pharmaceutically acceptable salt thereof, and ANTIBODY A, or a variant or derivative thereof, for the manufacture of a pharmaceutical preparation or medicament for the treatment of cancer that is resistant or refractive to treatment with an EGFR modulator or IGF1R inhibitor. In one embodiment, the cancer to be treated is a cancer identified above, which is hereby incorporated by reference in its entirety.

The present invention further provides the use of COMPOUND A for the treatment of cancer that is resistant or refractive to treatment with the IGF1R inhibitor ANTIBODY A.

The present invention comprises a pharmaceutical combination comprising the compound COMPOUND A, or a pharmaceutically acceptable salt thereof, and the IGF1R inhibitor ANTIBODY A, or a variant or derivative thereof, for use in the treatment of cancers that are resistant or refractive to currently-available therapies, e.g., EGFR amplified, IGF1R overexpressing, PIK3CA amplified, and/or PIK3CA mutated cancers that are resistant or refractive to EGFR inhibitors or IGF1R inhibitors, in a subject in need thereof.

Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages can be established using routine testing and procedures that are well known in the art.

The amount of combination of agents that can be combined with the carrier materials to produce separate dosage forms or a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage can vary depending on the compound used and the particular condition to be treated or prevented. In general, the use of the minimum dosage that is sufficient to provide effective therapy is preferred. Patients can generally be monitored for therapeutic effectiveness using assays suitable for the condition being treated or prevented, which will be familiar to those of ordinary skill in the art.

The dosage form can be prepared by various conventional mixing, comminution and fabrication techniques readily apparent to those skilled in the chemistry of drug formulations.

The oral dosage form containing the combination of agents or individual agents of the combination of agents can be in the form of micro-tablets enclosed inside a capsule, e.g. a gelatin capsule. For this, a gelatin capsule as is employed in pharmaceutical formulations can be used, such as the hard gelatin capsule known as CAPSUGEL®, available from Pfizer.

Many of the oral dosage forms useful herein contain the combination of agents or individual agents of the combination of agents in the form of particles. Such particles can be compressed into a tablet, present in a core element of a coated dosage form, such as a taste-masked dosage form, a press coated dosage form, or an enteric coated dosage form, or can be contained in a capsule, osmotic pump dosage form, or other dosage form.

The drug compounds of the present invention (for example, COMPOUND A, or a pharmaceutically acceptable salt thereof, and ANTIBODY A, or a variant or derivative thereof), are administered in the combinations (fixed or non-fixed), dosage forms (separate dosage forms or a co-formulation), pharmaceutical compositions and pharmaceutical formulations disclosed herein in a ratio in the range of 100:1 to 1:100. For example, the ratio of COMPOUND A:ANTIBODY A can be in the range of 1:100 to 1:1, for example, 1:100, 1:90, 1:80, 1:70, 1:60, 1:50, 1:40, 1:30, 1:20, 1:10, 1:5, 1:2, or 1:1. In another example, the ratio of ANTIBODY A:COMPOUND A can be in the range of 1:100 to 1:1, for example, 1:100, 1:90, 1:80, 1:70, 1:60, 1:50, 1:40, 1:30, 1:20, 1:10, 1:5, 1:2, or 1:1.

The optimum ratios, individual and combined dosages, and concentrations of the drug compounds that yield efficacy without toxicity are based on the kinetics of the active ingredients' availability to target sites, and are determined using methods known to those of skill in the art.

The pharmaceutical compositions or combinations provided herein (i.e., COMPOUND A, or a pharmaceutically acceptable salt thereof, and ANTIBODY A, or a variant or derivative thereof) can be tested in clinical studies. Suitable clinical studies can be, for example, open label, dose escalation studies in patients with cancer. Such studies prove in particular the synergism of the active ingredients of the combination of the invention. The beneficial effects on cancer can be determined directly through the results of these studies which are known as such to a person skilled in the art. Such studies can be, in particular, suitable to compare the effects of a monotherapy using the active ingredients and a combination of the invention. In one embodiment, the dose of COMPOUND A is escalated until the Maximum Tolerated Dosage is reached and ANTIBODY A is administered with a fixed dose. Alternatively, COMPOUND A is administered in a fixed dose and the dose of ANTIBODY A is escalated. Each patient can receive doses of the compounds either daily or intermittently. The efficacy of the treatment can be determined in such studies, e.g., after 12, 18 or 24 weeks of treatment, by evaluation of symptom scores every 4 to 6 weeks.

The administration of a combination therapy of the invention can result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit can be that lower and/or less frequent doses of one or both of the active ingredients of the combination of the invention can be used, which can diminish the incidence or severity of side-effects. This is in accordance with the desires and requirements of the patients to be treated.

It is one objective of this invention to provide a pharmaceutical combination that is therapeutically effective at treating or preventing cancer, e.g., a EGFR amplified, IGF1R overexpressing, PIK3CA amplified, and/or PIK3CA mutated cancer. In one embodiment of this combination, COMPOUND A and ANTIBODY A are administered in one combined unit dosage form or in two separate unit dosage forms. The unit dosage form can also be a fixed combination.

The pharmaceutical compositions for separate administration (or non-fixed dose) of both compounds, or for the administration in a fixed combination, i.e. a single composition comprising both compounds according to the invention can be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

In one embodiment, the present invention relates to a pharmaceutical composition or pharmaceutical formulation comprising (a) COMPOUND A, or a pharmaceutically acceptable salt thereof, and (b) ANTIBODY A, or a variant or derivative thereof, and optionally one or more pharmaceutically acceptable carriers.

In a further embodiment, the present invention further relates to a pharmaceutical composition or pharmaceutical formulation comprising (a) COMPOUND A, or a pharmaceutically acceptable salt thereof, and (b) ANTIBODY A, or a variant or derivative thereof, and optionally one or more pharmaceutically acceptable carriers, for use in the treatment of cancer.

In a further embodiment, the present invention relates to (a) a pharmaceutical combination comprising COMPOUND A, or a pharmaceutically acceptable salt thereof, and (b) a pharmaceutical composition comprising ANTIBODY A, or a variant or derivative thereof, administered in separate pharmaceutical compositions to a subject in need thereof.

Formulations

The drug combinations provided herein can be formulated by a variety of methods apparent to those of skill in the art of pharmaceutical formulation. As discussed above, the active ingredients of the combination (e.g., COMPOUND A and ANTIBODY A) can be formulated into the same pharmaceutical composition or into separate pharmaceutical compositions for individual administration. Suitable formulations include, for example, tablets, capsules, press coat formulations, intravenous solutions or suspensions, and other easily administered formulations.

One or both combination partners can be administered in a pharmaceutical formulation comprising one or more pharmaceutically acceptable carriers. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Suitable pharmaceutical formulations can contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In accordance with the present invention, a therapeutically effective amount of each of the combination partners of the combination of the invention can be administered simultaneously or sequentially and in any order, and the components can be administered separately or as a fixed combination. Alternatively, an amount, which is jointly therapeutically effective for the treatment of cancer, of each combination partner of the combination of the invention can be administered simultaneously or sequentially and in any order, and the components can be administered separately or as a fixed combination.

For example, the method of treating a disease according to the invention can comprise (i) administration of the first agent in free or pharmaceutically acceptable salt form and (ii) administration of the second agent in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention can vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition. A clinician or physician of ordinary skill can also readily determine the effective dosage using the Response Evaluation Criteria In Solid Tumors (RECIST) guidelines (see e.g., Therasse et al. 2000, JNCI 92:2, 205, which is hereby incorporated by reference in its entirety).

Suitable dosages for COMPOUND A used in the methods described herein may range from about 0.05 to about 50 mg of COMPOUND A per kilogram body weight of the recipient ("mg/kg") per day; preferably about 0.1-25 mg/kg/day, more preferably from about 0.5 to 10 mg/kg/day. Thus, for administration to a 70 kg person, the dosage range would most preferably be about 35-700 mg per day.

Suitable dosages for ANTIBODY A, or a variant or derivative thereof, used in the methods described herein are on the order of about 1 mg/kg to about 100 mg/kg, (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 95, or 100 mg/kg). In a preferred embodiment, ANTIBODY A, or a variant or derivative thereof, is administered to a subject at a dosage of about 9, 12 or 20 mg/kg.

Suitable administration frequencies for COMPOUND A or ANTIBODY A, or a variant or derivative thereof, used in the methods described herein are on the order of about 10 times per day to about once per six months (e.g., about 10, 9, 8, 7, 6, 5, 4, 3, 2, 1 times per day to about 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 times per month). Specific examples of dosing frequencies are once per day, once per week, once per two weeks, once per three weeks, and once per month. The administration frequency for COMPOUND A can be different than the administration frequency of ANTIBODY A, or a variant or derivative thereof, or they can be the same. The administration frequency for COMPOUND A and/or ANTIBODY A, or a variant or derivative thereof, can be different for different patients, even among patients with the same or similar disease to be treated. The administration frequency for COMPOUND A and/or ANTIBODY A, or a variant or derivative thereof, can be changed for a patient during the course of treatment.

In one embodiment, from about 0.5 to 10 mg/kg/day of COMPOUND A is administered orally to a subject. In another embodiment, ANTIBODY A, or a variant or derivative thereof, is administered intravenously twice per month at between about 9 and about 20 mg/kg.

The invention is further illustrated by the following examples. The examples should not be construed as further limiting. The beneficial effects of the combination of the invention can also be determined by other test models known to the person skilled in the pertinent art.

Example 1

Synthesis of COMPOUND A

The synthesis of COMPOUND A is described in International Patent Application WO2010/029082, which is incorporated by reference in its entirety. The synthesis of this compound is described below.

(S)-Pyrrolidine-1,2-dicarboxylic acid 2-amide 1-{[5-(2-tert-butyl-pyridin-4-yl)-4-methyl-thiazol-2-yl]-amide}

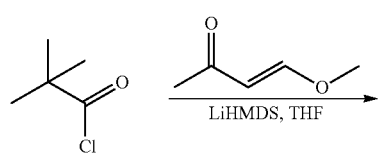

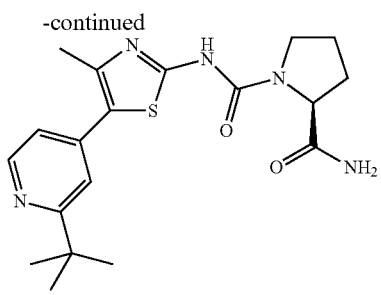

Example 1

Et₃N (1.54 mL, 11.1 mmol, 3 eq) is added to a solution of imidazole-1-carboxylic acid [5-(2-tert-butyl-pyridin-4-yl)-4-methyl-thiazol-2-yl]-amide (Step 1.1) (1.26 g, 3.7 mmol) and L-prolinamide (0.548 g, 4.8 mmol, 1.3 eq) in DMF (25 mL), under an argon atmosphere. The reaction mixture is stirred for 14 h at rt, quenched by addition of a saturated solution of NaHCO₃, and extracted with EtOAc. The organic phase is washed with a saturated solution of NaHCO₃, dried (Na₂SO₄), filtered and concentrated. The residue is purified by silica gel column chromatography (DCM/MeOH, 1:0→94:6), followed by trituration in Et₂O to afford 1.22 g of the title compound as an off-white solid: ESI-MS: 388.1 [M+H]⁺; $t_R$=2.35 min (System 1); TLC: $R_f$=0.36 (DCM/MeOH, 9:1). ¹H NMR (400 MHz, DMSO-d6) δ(ppm): 1.32 (s, 9H) 1.75-1.95 (m, 3H) 1.97-2.13 (m, 1H) 2.39 (s, 3H) 3.38-3.50 (m, 1H) 3.52-3.65 (m., 1H) 4.10-4.40 (m, 1H) 6.94 (br. s., 1H) 7.22 (d, 1H) 7.30-7.48 (m, 2H) 8.49 (d, 1H) 10.87 (br. s., 1H)

Step 1.1: Imidazole-1-carboxylic acid [5-(2-tert-butyl-pyridin-4-yl)-4-methyl-thiazol-2-yl]-amide

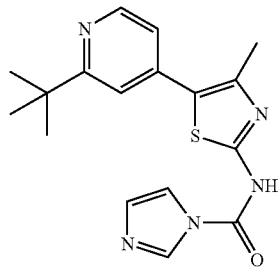 [SMILES: Cc1nc(NC(=O)n2ccnc2)sc1-c1ccnc(C(C)(C)C)c1]

A mixture of 5-(2-tert-butyl-pyridin-4-yl)-4-methyl-thiazol-2-ylamine (Step 1.2) (1 g, 4.05 mmol) and 1,1'-carbonyldiimidazole (0.984 g, 6.07 mmol, 1.5 eq) in DCM (50 mL) is stirred for 4 h at reflux and allowed to cool. The resulting precipitate is collected by filtration to provide 1.26 g of the title compound as white solid: ESI-MS: 340.2 [M−H]⁻; $t_R$=2.85 min (System 1).

Step 1.2: 5-(2-tert-Butyl-pyridin-4-yl)-4-methyl-thiazol-2-ylamine

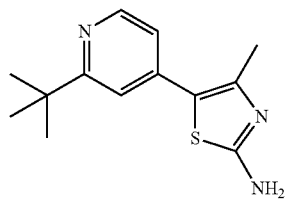 [SMILES: Cc1nc(N)sc1-c1ccnc(C(C)(C)C)c1]

A mixture of N-[5-(2-tert-butyl-pyridin-4-yl)-4-methyl-thiazol-2-yl]-acetamide (Step 1.3) (2 g, 7 mmol), a 6N aqueous solution of HCl (10 mL) and EtOH (50 mL) is stirred for 2 h at 85° C., allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (DCM/MeOH, 1:0→96:4) to afford 1.21 g of the title compound as a yellow solid: ESI-MS: 248.1 [M+H]⁺; TLC: $R_f$=0.36 (DCM/MeOH, 9:1).

Step 1.3: N-[5-(2-tert-Butyl-pyridin-4-yl)-4-methyl-thiazol-2-yl]-acetamide

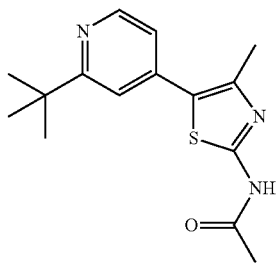 [SMILES: CC(=O)Nc1nc(C)c(-c2ccnc(C(C)(C)C)c2)s1]

A mixture of 2-acetamido-4-methylthiazole (1.2 g, 7.7 mmol, 1.1 eq), cesium carbonate (4.55 g, 14 mmol, 2 eq), tri-tert-butylphosphinium tetrafluoroborate (0.406 g, 1.4 mmol, 0.2 eq), palladium (II) acetate (0.15 g, 0.7 mmol, 0.1 eq) and 4-bromo-2-tert-butyl-pyridine (Step 1.4) (1.5 g, 7 mmol) in DMF (50 mL) is stirred for 1.5 h at 90° C. under an argon atmosphere, allowed to cool, quenched by addition of a saturated solution of NaHCO₃ and filtered through a pad of celite. The filtrate is extracted with EtOAc. The organic phase is washed with a saturated solution of NaHCO₃, dried (Na₂SO₄), filtered and concentrated. The residue is purified by silica gel column chromatography (DCM/MeOH, 1:0→97:3) to afford 2.02 g of the title compound as a yellow solid: ESI-MS: 290.1 [M+H]⁺; TLC: $R_f$=0.35 (DCM/MeOH, 9:1).

Step 1.4: 4-Bromo-2-tert-butyl-pyridine

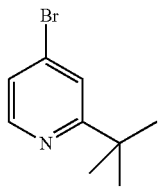

A mixture of 2-tert-butyl-1H-pyridin-4-one (Step 1.5) (4.25 g, 28 mmol) and POBr₃ (8.88 g, 31 mmol, 1.1 eq) is heated to 120° C., stirred for 15 min, allowed to cool, quenched by addition of a saturated solution of NaHCO₃ and extracted with DCM/MeOH (9:1, v/v). The organic phase is washed with a saturated solution of NaHCO₃, dried (Na₂SO₄), filtered and concentrated. The residue is purified by silica gel column chromatography (Hex/EtOAc, 95:5) to afford 5.18 g of the title compound as a yellow oil: ESI-MS: 214.0/216.0 [M+H]⁺; t_R=2.49 min (System 1); TLC: R_f=0.35 (Hex/EtOAc, 1:1).

Step 1.5: 2-tert-Butyl-1H-pyridin-4-one

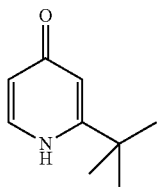

A mixture of 2-tert-butyl-pyran-4-one (Step 1.6) (5.74 g, 37.7 mmol) and a 30% aqueous solution of ammonium hydroxide (100 mL) is stirred for 1 h at reflux, allowed to cool and concentrated. The residue is triturated with MeOH (200 mL) and filtered. The filtrate is concentrated and the residue purified by silica gel column chromatography (DCM/MeOH/NH₃$^{aq}$, 94:5:1→92:7:1) to afford 4.46 g of the title compound as a yellow solid: ESI-MS: 152.0 [M+H]⁺; t_R=1.45 min (System 1); TLC: R_f=0.11 (DCM/MeOH, 9:1).

Step 1.6: 2-tert-Butyl-pyran-4-one

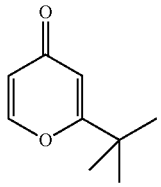

A mixture of 5-hydroxy-1-methoxy-6,6-dimethyl-hepta-1,4-dien-3-one (Step 1.7) (6.8 g, 36.9 mmol) and TFA (5.65 mL, 74 mmol, 2 eq) in benzene (250 mL) is stirred for 14 h at rt and concentrated. Purification of the residue by silica gel column chromatography (Hex/EtOAc, 1:0→75:25) provides 5.74 g of the title compound as a yellow oil: ESI-MS: 153.1 [M+H]⁺; t_R=3.21 min (System 1); TLC: R_f=0.22 (Hex/EtOAc, 1:1).

Step 1.7: 5-Hydroxy-1-methoxy-6,6-dimethyl-hepta-1,4-dien-3-one

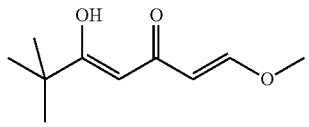

LiHMDS (1M in THF, 100 mL, 2 eq) is added dropwise to a cold (−78° C.) solution of 4-methoxy-3-buten-2-one (10 mL, 100 mmol, 2 eq) in THF (400 mL). After a 30 min stirring at −78° C., a solution of pivaloyl chloride (6.12 mL, 50 mmol) in THF (100 mL) is added. The resulting mixture is allowed to warm to rt over 2 h and quenched by addition of a saturated solution of NH₄Cl. THF is removed under vacuum. The concentrated mixture is extracted with Et₂O. The organic phase is washed with brine, dried (Na₂SO₄), filtered and concentrated. The residue is purified by silica gel column chromatography (Hex/EtOAc, 1:0→85:15) to afford 6.83 g of the title compound as a yellow oil: ESI-MS: 185.1 [M+H]⁺; TLC: R_f=0.87 (Hex/EtOAc, 1:1).

(S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide)

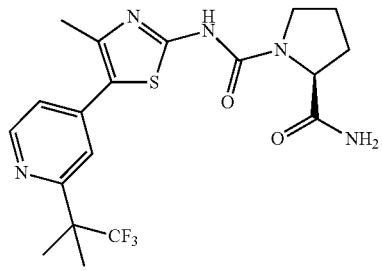 [SMILES: Cc1nc(NC(=O)N2CCC[C@H]2C(N)=O)sc1-c1ccnc(C(C)(C)C(F)(F)F)c1]

The title compound is prepared in analogy to the procedure described in Example 1 but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, the reaction mixture is stirred for 2.5 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride (Step 12.1) is used.

Title compound: ESI-MS: 442.0 [M+H]⁺; t_R=3.02 min (System 1); TLC: R_f=0.35 (DCM/MeOH, 9:1). ¹H NMR (400 MHz, DMSO-d6) δ(ppm): 1.60 (s, 6H) 1.70-1.95 (m, 3H) 1.99-2.16 (m, 1H) 2.40 (s, 3H) 3.38-3.51 (m, 1H) 3.51-3.69 (m, 1H) 4.10-4.40 (m, 1H) 6.95 (br. s., 1H) 7.39 (d, 2H) 7.53 (s, 1H) 8.58 (d, 1H) 10.93 (br. s., 1H)

In an alternative procedure the title compound is prepared in analogy to the procedure described in Example 1 but with the following modifications: N,N-Dimethylacetamide is used instead of DMF and the mixture is stirred at 65° C. for 2 h. In Step 1.1, phenyl chloroformate (added slowly) is used instead of 1,1'-carbonyldiimidazole and the reaction is carried out in THF in the presence of N,N-diethyl-isopropylamine at room temperature (1.5 h). In Step 1.2, the reaction mixture is heated under stirring for 5 h under (reflux) and extracted with EtOAc after being quenched. In Step 1.3, the reaction mixture is stirred for 2 h at 100° C. In Step 1.4, the reaction is run in toluene using 1.1 equivalents of POBr₃ and 1.1 equivalents of tripropylamine and the mixture is stirred for 2 h at 80° C. and extracted with EtOAc after being quenched. In Step 1.5, the reaction mixture is stirred for 1 h at 65° C. and trituration in MeOH is not performed. In Step 1.6, toluene is used instead of benzene and the crude product is not purified. In Step 1.7, 3,3,3-trifluoro-2,2-dimethyl-propionyl chloride (Step 12.1) is used.

Example 2

Phase Ib/II Open-Label, Multi-Center Study of the Combination of Alpha-Isoform Specific PI3K Inhibitor COMPOUND A and Insulin-Like Growth Factor-1 Receptor (IGF-1R) Inhibitor ANTIBODY A in Adult Patients with Selected Advanced Solid Tumors A multi-center, open-label, phase Ib/II study is conducted evaluating the efficacy and safety of the combination of the alpha-isoform specific PI3K inhibitor COMPOUND A and the Insulin-like growth factor-1 receptor (IGF-1R) inhibitor ANTIBODY A in adult patients with selected advanced solid tumors. First, a dose-escalation Phase Ib study is conducted to estimate the maximal terminal dose(s) (MTDs) and/or to identify the recommended Phase II dose(s) (RP2D) for the combination of the alpha-isoform specific PI3K inhibitor COMPOUND A and Insulin-like growth factor-1 receptor (IGF-1R) inhibitor ANTIBODY A in patients with PIK3CA mutated or amplified solid tumors. Second, a Phase II study is conducted to assess the antitumor activity and safety of the alpha-isoform specific PI3K inhibitor COMPOUND A and Insulin-like growth factor-1 receptor (IGF-1R) inhibitor ANTIBODY A in select patients having cancer, particularly those patients having PIK3CA mutated or amplified hormone receptor positive breast cancer or those patients having PIK3CA mutated or amplified ovarian cancer.

Dose-Escalation Study

Patients with advanced solid tumors with documented somatic PIK3CA mutations or amplifications in tumor tissue such as hormone receptor positive breast carcinoma, ovarian carcinoma or other tumors are enrolled. Each enrolled patient is determined to satisfy the specific inclusion/exclusion criteria set forth below. For this dose-escalation phase of the study, at least 10-15 patients are enrolled.

The first dose of either COMPOUND A or ANTIBODY A defines Cycle 1 Day 1. All treatment cycles have 28 days. There are no delays between cycles. Patients are administered a starting dose for the combination of 200 mg once daily (Q.D.) COMPOUND A and 12 mg/kg once every second week (Q2W) ANTIBODY A. COMPOUND A is administered orally, and ANTIBODY A is administered as a solution for intravenous infusion. Patients are dosed on a flat scale with COMPOUND A, and patients are dosed with ANTIBODY A according to body weight. On infusion days, COMPOUND A is administered orally immediately upon completion of the ANTIBODY A infusion.

In one study alternative, COMPOUND A is administered orally twice daily (BID) for the same total daily dosage of COMPOUND A. Doses are administered approximately 12 hours apart. This study alternative is not required to assess the dose-escalation or safety and efficacy for the COMPOUND A and ANTIBODY A combination.

During dose escalation, only one study drug is escalated at a time and the maximum inter-cohort dose escalation is limited to 100% (ie., up to 100% and 0% increase for ANTIBODY A and COMPOUND A respectively, or 0% and up to 100% increase for ANTIBODY A and COMPOUND A respectively). The following dose increments may be evaluated:

| Dose Level | COMPOUND A mg QD | ANTIBODY A mg/kg Q2W |
|---|---|---|
| −1b* | 100 | 12 |
| −1a* | 200 | 9 |
| Starting Dose level 1 | 200 | 12 |
| 2 | 300 | 12 |
| 3 | 300 | 20 |
| 4 | 400 | 20 |

*"a" and "b"-dose levels may be explored in parallel.

The dose escalation part of the study is guided by a Bayesian Logistic Regression Model (BLRM). At all decision time points, the adaptive BLRM permits alterations in the dose increments based on the observed dose-limiting toxicities (DLTs).

DLTs are assessed using the National Cancer Institute (NCI) Common Toxicity Criteria for Adverse Events (CTCAE), version 4.03. A "DLT" is defined as an adverse event or abnormal laboratory value assessed as at least possibly related to the study medication, occurs≤28 days following the first dose of COMPOUND A and ANTIBODY A (Cycle 1) and meets any of the following criteria:

| TOXICITY | DLT CRITERIA |
|---|---|
| Blood and lymphatic system disorders | Anemia CTCAE Grade ≥3<br>Febrile neutropenia CTCAE Grade ≥3 (ANC <1.0 × $10^9$/L, fever ≥38.5° C.)<br>Thrombocytopenia CTCAE Grade 3 for >7 consecutive days requiring platelet transfusion<br>Thrombocytopenia CTCAE Grade 4 |
| Cardiac disorders | Decrease of left ventricular ejection fraction >10% compared to baseline and the LVEF is below the institution's LLN[a]<br>Left ventricular systolic dysfunction CTCAE Grade ≥3<br>Other cardiac disorders CTCAE Grade ≥3<br>Clinical signs of cardiac disease, such as unstable angina or myocardial infarction, or Troponin CTCAE Grade 3 (confirmed with a repeat Troponin within 24 hrs) |
| Vascular disorders/Hypertension | Persistent hypertension CTCAE Grade ≥3 requiring more than one drug or more intensive therapy than previously<br>Thromboembolic event CTCAE Grade 2 requiring full-dose anticoagulation therapy<br>Thromboembolic event CTCAE Grade ≥3 |
| General disorders and administration site conditions | Fatigue CTCAE Grade 3 for >7 consecutive days |
| Skin and subcutaneous tissue disorders:[b] Rash and/or photosensitivity | Rash or photosensitivity CTCAE Grade 3 for >7 consecutive days despite skin toxicity treatment<br>Rash or photosensitivity CTCAE Grade 4 |

| TOXICITY | DLT CRITERIA |
|---|---|
| Metabolism and nutrition disorders: Hyperglycemia[a] | Hyperglycemia Grade 3 (FPG 250 - 399 mg/dL; 13.9-22.2 mmol/L) (confirmed with a repeat FPG within 24 hrs) for >5 consecutive days despite anti-diabetic treatment<br>Hyperglycemia Grade 4 (FPG ≥400 mg/dL; ≥22.3 mmol/L)<br>Hyperglycemia leading to diabetic keto-acidosis, hospitalization for IV insulin infusion, or non-ketotic coma |
| GI disorders[b] | Diarrhea CTCAE Grade ≥3 for ≥48 hrs, despite the use of anti-diarrhea therapy<br>Nausea/vomiting CTCAE Grade ≥3 for ≥48 hrs, despite the use of anti-emetic therapy<br>Pancreatitis CTCAE Grade ≥3 |
| Investigations[c] | Blood bilirubin[d] CTCAE Grade 2 for >7 consecutive days<br>Blood bilirubin[d] CTCAE Grade ≥3<br>AST or ALT 3 x upper limit of normal in conjunction with blood bilirubin[d] 2 x upper limit of normal of any duration<br>AST or ALT CTCAE Grade ≥3 in conjunction with blood bilirubin[d] CTCAE Grade ≥2 of any duration for patients with elevated AST, ALT or blood bilirubin at baseline or documented liver metastases<br>AST or ALT CTCAE Grade 3 for >7 consecutive days<br>AST or ALT CTCAE Grade 4<br>Serum alkaline phosphatase CTCAE Grade 4<br>Serum lipase and/or serum amylase (asymptomatic) CTCAE Grade 3 >7 consecutive days<br>Serum lipase and/or serum amylase (asymptomatic) CTCAE Grade 4<br>Serum creatinine CTCAE Grade ≥3<br>Serum CK/CPK CTCAE Grade 3 for >7 consecutive days<br>Serum CK/CPK CTCAE Grade 4<br>ANC CTCAE Grade 3 for >7 consecutive days<br>ANC CTCAE Grade 4<br>Platelet count CTCAE Grade 3 for >7 consecutive days and/or with signs of bleeding requiring platelet transfusion<br>Platelet count CTCAE Grade 4<br>ECG QTc interval prolonged CTCAE Grade ≥3 (refers to QTcF >500 msec as measured by manual review and confirmed by a repeat measurement |
| Ear and labyrinth disorders | New onset hearing impaired CTCAE Grade ≥3 if hearing loss cannot be clearly attributed to another cause (e.g. acoustic trauma) |
| Other hematologic & non-hematologic toxicities | Any other CTCAE Grade ≥3 toxicity except:<br>Lymphocyte count decreased (lymphopenia) CTCAE Grade ≥3 unless clinically significant |

[a]Not according to CTCAE v4.03
[b]Patients will not initially receive prophylactic treatment for skin toxicity or nausea/vomiting during Cycle 1. However, prophylactic treatment may be initiated in all patients at the dose level where these toxicities have been observed at the discretion of the investigator
[c]For any CTCAE Grade 4, or CTCAE Grade 3 hepatic toxicity that does not resolve within 7 days to CTCAE Grade ≤1 (or CTCAE Grade ≤2 if liver infiltration with tumor present), an abdominal CT scan has to be performed to assess if it is related to disease progression.
[d]Refers to total bilirubin.

Whenever a patient experiences a DLT, treatment with the study drug combination is interrupted and the toxicity is followed up.

The "MTD" is defined as the highest combination drug dosage not causing medically unacceptable DLT in more than 35% of the treated patients in the first cycle of treatment. Since several combinations may correspond to this definition, more than one MTD may be identified with different doses of the study drugs. The applied adaptive Bayesian methodology provides an estimate of the combinations of COMPOUND A and ANTIBODY A not exceeding the MTD. Typically the MTD is a tested dose with maximum probability of targeted toxicity (DLT rate between 16%-35%). The use of EWOC principle limits the risk that a potential next dose will exceed the MTD.

For the dose-escalation phase of the study, dosage pairs are explored until the MTD and/or RP2D is determined and/or until it is considered that there is no further benefit from further increasing the dose. For purposes of dose escalation decisions, each cohort consists of 3 to 6 newly enrolled patients treated at the specified dose levels. Patients must complete a minimum of 1 cycle of treatment with the minimum safety evaluation and drug exposure or have had a DLT within the first cycle of treatment to be considered evaluable for dose escalation decisions. Dose escalation decisions occur when the cohort of patients meets these criteria. If only 2 of the 3 patients in a cohort are evaluable and neither patient experiences a treatment-related toxicity>CTCAE grade 1, dose escalation decisions are considered. If needed to better define the dose-toxicity relationship, additional patients may be enrolled to the current combination dose level, to a preceding combination dose level, or to an intermediate combination dose level before proceeding with further dose escalation. In general, if toxicities CTCAE Grade≥2 are observed in at least two patients in the previous cohort, then dose escalation for the combination partners are limited to <100%. However, for certain toxicities, such as hematologic toxicity (e.g., neutropenia, thrombocytopenia), and toxicities not associated with end-organ damage (e.g., nausea, pain, headache, fever), toxicity CTCAE Grade≥2 must be observed in at least two thirds of the patients in the previous cohort, before dose escalation is limited to <100%.

If the first 2 patients in a cohort experience a DLT, further enrollment to that cohort is stopped and the BLRM is updated with this new information. Re-evaluation of the available safety, PK, and PD data occurs. By incorporating information gained at the preceding dose levels, additional patients may be enrolled at this dose level or a lower dose level and if the BLRM predicts that the risk for this dose to exceed the MTD remains below 25% (EWOC).

Dose escalation continues until identification of the MTD(s) or a suitable lower combination dose for phase II. This occurs when the following conditions are met:
1. at least 6 patients are treated at this combination dose
2. this combination dose satisfies one of the following conditions:
   a. the posterior probability of targeted toxicity at this combination dose exceeds 50% and is the highest among potential doses, or
   b. a minimum of 15 patients are already treated in the trial
3. it is the dose recommended for the next cohort of patients (either per the model or by review of all clinical data).

If a decision is made to escalate to a higher dose level but one or more additional patient(s) treated at the preceding dose level experiences a DLT during the first cycle of treatment, then the BRLM is updated with this new information before any additional patients are enrolled at that higher dose level. Patients ongoing continue treatment at their assigned dose levels.

Intrapatient dose escalation is not permitted with the first 4 cycles of treatment. Each cycle is 28 days. Only one of the investigational study drugs is escalated at any one time. In order for a patient to be treated at a higher dose of either COMPOUND A or ANTIBODY A, he or she must tolerate the lower dose pair for at least four cycles of therapy, e.g. he or she must not experience at the lower dose pair originally assigned a toxicity of CTCAE Grade≥2 for which relationship to study drug cannot be ruled out. Moreover, the new, higher dose pair with which the patient is to be treated must be a dose pair that completes evaluation and that does not exceed the MTD estimated by the BLRM given all available data. There is no set limit to the number of times a patient may have his or her dose of either COMPOUND A or ANTIBODY A increased.

Patients are discontinued from the study if: (a) a dose delay of >21 consecutive days of COMPOUND A and/or more than 2 consecutive doses of ANTIBODY A from the intended day of the next scheduled dose, or (b) adverse events or an abnormal laboratory value. Any patient whose treatment is interrupted or permanently discontinued due to an adverse event or clinically significant laboratory issue is followed up for toxicities at least once a week for 4 weeks. A maximum of two (2) dose reductions are allowed and, upon dose reduction, no dose re-escalation is permitted. Dose reduction below 50 mg QD COMPOUND A is not permitted, and dose reduction below 9 mg kg Q2W ANTIBODY A is not permitted. For each patient, once a dose escalation has occurred, the dose level may not be re-escalated during subsequent treatment cycles.

Inclusion and Exclusion Criteria:

The inclusion criteria for the patients are those that satisfy all of the following:
1. Written informed consent is obtained prior to any screening procedures.
2. Patients aged≥18 years (male or female).
3. Patients with the following histologically/cytologically-confirmed advanced solid tumors with documented somatic PIK3CA mutations or amplifications in tumor tissue (based on available local documentation, i.e. pathology report at the site), for whom according to the assessment of the investigator no standard therapy exists:
   (a) For dose escalation (phase Ib) only:
      Hormone receptor positive breast carcinoma
      Ovarian carcinoma
      Other tumors upon agreement
   (b) For phase II Arm 1 only:
      Patients with PIK3CA mutated or amplified hormone receptor positive breast carcinoma
   (c) For phase II Arm 2 only:
      Patients with PIK3CA mutated or amplified ovarian carcinoma.
4. Fresh tumor biopsy must be collected at baseline.
5. Patients must have relapsed or progressed following standard therapy or patients for whom no standard anticancer therapy according to investigator assessment exists.
6. Measurable disease as determined by RECIST v1.1. Target lesions in previously irradiated areas are not selected unless there is clear evidence of progression in such lesions.
7. World Health Organization (WHO)/Eastern Cooperative Oncology Group (ECOG)) Performance Status (PS)≤2.
8. Adequate organ function and laboratory parameters as defined by:
   Absolute neutrophil count (ANC)≥1.5×10$^9$/L
   Hemoglobin (Hgb)≥9 g/dl
   Platelets (PLT)≥100×10$^9$/L without transfusions within 21 days before first treatment
   AST/SGOT and/or ALT/SGPT≤2.5×ULN (upper limit of normal) or ≤5×ULN if liver metastases are present
   Serum bilirubin≤1.5×ULN
   Serum creatinine≤1.5×ULN or calculated or directly measured CrCl≥50% LLN (lower limit of normal).
9. Recovery from all Adverse Eventss of previous anti-cancer therapies, including surgery and radiotherapy, to baseline or to CTCAE Grade≤1, except for alopecia.
10. Negative serum pregnancy (β-hCG) test within 72 hrs before starting study treatment in all pre-menopausal women and women<12 months after the onset of menopause.

The exclusion criteria for the patients are the following:
1. Prior therapy with PI3K inhibitor or IGF-1R inhibitor.
2. Patients with known history of severe infusion reactions to monoclonal antibodies.
3. Patients with primary Central Nervous System (CNS) tumor or CNS tumor involvement, unless the patient has a metastatic CNS tumor and the following:
   4 weeks from prior therapy completion (including radiation and/or surgery) and,
   Clinically stable with respect to the CNS tumor at the time of study entry and,
   Not receiving steroid therapy and,
   Not receiving anti-convulsive medications (that were started for brain metastases).
4. Patients who have received prior systemic anti-cancer treatment within the following time frames:
   Cyclical chemotherapy within a period of time that is shorter than the cycle length used for that treatment (e.g. 6 weeks for nitrosourea, mitomycin-C) prior to starting study treatment
   Biologic therapy (e.g. antibodies), continuous or intermittent small molecule therapeutics, or any other investigational agents within a period of time which is ≤5 $t_{1/2}$ or ≤4 weeks (whichever is shorter) prior to starting study treatment.
5. Patients who have received radiotherapy≤4 weeks prior to starting study drug, with exception of palliative radiotherapy, who have not recovered from side effects of such therapy and/or from whom≥30% of the bone marrow was irradiated.
6. Patients who have undergone major surgery≤4 weeks prior to starting study treatment or who have not recovered from side effects of such procedure.
7. History of thromboembolic event requiring full-dose anti-coagulation therapy any time prior to enrollment.
8. Clinically significant cardiac disease or impaired cardiac function, such as:
   Clinically significant heart disease such as CHF requiring treatment (NYHA Grade≥2), LVEF<50% as determined by MUGA scan or echocardiogram (ECHO), or uncontrolled arterial hypertension defined by blood pressure>140 (systolic)/100 (diastolic) mmHg at rest (average of 3 consecutive readings)
   History or current evidence of clinically significant cardiac arrhythmias, atrial fibrillation and/or conduction abnormality, e.g. congenital long QT syndrome, high-Grade/complete AV-blockage
   History/evidence of acute coronary syndromes (including myocardial infarction, unstable angina, coronary artery bypass graft (CABG), coronary angioplasty, or stenting), <6 months prior to screening
   QTcF>480 msec on screening ECG
   Complete left bundle branch block
   Right bundle branch block+left anterior hemiblock (bifascicular block).
9. Patients with diabetes mellitus requiring insulin treatment or with fasting plasma glucose>140 mg/dL (7.8 mmol/L).
10. Patients with peripheral neuropathy CTCAE Grade≥2.
11. Patients with diarrhea CTCAE Grade≥2.
12. Patients with acute or chronic pancreatitis.
13. Any other condition that would, in the Investigator's judgment, contraindicate the patient's participation in the clinical study due to safety concerns or compliance with the clinical study procedures, e.g. infection/inflammation, intestinal obstruction, unable to take oral medication, social/psychological complications.
14. Impaired Gastrointestinal (GI) function or GI disease (e.g. ulcerative disease, uncontrolled nausea, vomiting, diarrhea, malabsorption syndrome, or small bowel resection).
15. Patients who are currently receiving medication with a known risk of prolonging the QT interval or inducing Torsades de Pointes and the treatment cannot either be discontinued or switched to a different medication prior to starting study drug treatment.
16. Patients treated with hematopoietic colony-stimulating growth factors (e.g. G-CSF, GM-CSF, M-CSF)≤2 weeks prior to starting study drug. Erythropoietin or darbepoetin is allowed as long as it has been initiated at least 2 week prior to study enrollment.
17. Patients who have received systemic corticosteroids≤2 weeks prior to starting study drug, or who have not fully recovered from side effects of such treatment.
18. History of another malignancy within 2 years, except cured basal cell carcinoma of the skin or excised carcinoma in situ of the cervix.
19. Known positive serology for HIV, active Hepatitis B, and/or active Hepatitis C infection.
20. Pregnant or nursing (lactating) women, where pregnancy is defined as the state of a female after conception and until the termination of gestation, confirmed by a positive hCG laboratory test (>5 mIU/mL).
21. Women of child-bearing potential, defined as all women physiologically capable of becoming pregnant, are not allowed to participate in this study UNLESS they are using highly effective methods of contraception throughout the study and for 3 months after study drug discontinuation.
22. Sexually active males must use a condom during intercourse while taking the drugs and for 6 months after stopping treatment and should not father a child in this period.

Efficacy Study

Following MTD/RP2D declaration, patients are enrolled in two Phase II arms to assess efficacy of the combination: (a) Arm 1—patients with PIK3CA mutated or amplified breast carcinoma, and (b) Arm 2—patients with PIK3CA mutated or amplified ovarian carcinoma Approximately 20-30 patients are enrolled in each of Arm 1 and Arm 2. If more than one dose combination or regimen is defined in the dose-escalation phase, additional Phase II arms may be added to the Efficacy Study.

Patients are administered a suitable dosage of the combination of COMPOUND A and ANTIBODY A, as defined in the dose-escalation Phase Ib study.

Efficacy of the administered combination of COMPOUND A and ANTIBODY A is assessed by comparison of the tumor progression from baseline/screening. All potential sites of tumor lesions are assessed at baseline/screening by radiologic techniques (e.g., CT or MRI imaging), or where appropriate by physical examination (e.g. subcutaneous nodules and measurable cutaneous lesions). The methods of measurement are following the RECIST version 1.1 criteria for solid tumors. While enrolled in the study, follow-up tumor assessments are performed after completion of 8 weeks of treatment (Cycle 3 Day 1), 16 weeks of treatment (Cycle 5 Day 1), and every 8 weeks thereafter and at the end of treatment visit. Further efficacy factors are assessed by safety and tolerability assessments, physical examinations (including examination of general appearance, skin, neck (including thyroid), eyes, ears, nose, throat, lungs, heart, abdomen, back, lymph nodes, extremities, vascular and neurological, and potentially rectal, external genitalia, breast, and pelvic exams), vital signs (including temperature, respiration rate, sitting blood pressure and sitting pulse (heart rate)), and performance status. Performance status is assessed by the Eastern Cooperative Group (ECOG) (WHO) PS scale as follows:

| | |
|---|---|
| Grade 0 | Fully active, able to carry on all pre-disease performance without restriction. |
| Grade 1 | Restricted in physically strenuous activity but ambulatory and able to carry out work of a light or sedentary nature, e.g. light housework, office work. |
| Grade 2 | Ambulatory and capable of all self-care but unable to carry out any work activities. Up and about more than 50% of waking hours. |
| Grade 3 | Capable of only limited self-care, confined to bed or chair more than 50% of waking hours. |
| Grade 4 | Completely disabled. Cannot carry on any self-care. Totally confined to bed or chair. |

Note:
Grade 5 (dead) was removed from this table. This information will be collected on a separate eCRF page.

Patients are treated until progression of disease, unacceptable toxicity develops, or withdrawal of informed consent, whichever occurs first. All patients are followed up. At minimum, patients must complete a safety follow-up assessment 30 days after the last dose of the study treatment, including collection of information about anti-neoplastic therapies taken since discontinuation and adverse events. Depending on the outcome of these assessments, patients who may have further safety follow-up for those patients who test positive for neutralizing antibodies until test becomes negative or returns to baseline, or up to 12 months from safety follow-up visit, whichever is first. In addition, patients who have not progressed at the time of discontinuation from the study treatment should have (a) disease progression follow-up for those patients who have not progressed at time of discontinuation of study treatment approximately every 8 weeks (±7 days) until disease progression or initiation of subsequent anticancer therapy, or death, whichever occurs first, and (b) survival follow-up every 4 months until death or up to 12 months after last patient last treatment.

The study ends when the treatment period, safety period, safety follow-up, disease follow-up and survival follow-up (only for the Phase II Efficacy Study) have ended for all patients, or when the study is terminated early. However, the safety and efficacy of the combination is assessed and determined with interim clinical trial data obtained prior to study end.

Example 3

Targeting PIK3CA Mutant Breast Cancer with the Combination of Alpha-Isoform Specific PI3K Inhibitor, COMPOUND A, and IGF1-R Antibody, ANTIBODY A The experiments below examined whether PIK3CA inhibition would also trigger IGF1-R/IRS signaling. In addition, the combination of alpha-isoform specific PI3K inhibitor, COMPOUND A, and a fully human antibody against IGF1-R, ANTIBODY A, preclinically against a PIK3CA mutant breast cancer model, MCF7, was explored. The luminal breast cancer cell line MCF7 carries an activitating PIK3CA somatic mutation. The data indicate that IGF1-R/IRS signaling is activated upon PIK3CA inhibition. COMPOUND A exhibited concentration-dependent tumor growth inhibition in vitro. ANTIBODY A alone had modest inhibitory activity. The combination of COMPOUND A and ANTIBODY A inhibited MCF7 growth synergistically in vitro (Experiment 1). This combination was further tested in an MCF7 xenograft in mice (Experiment 2). COMPOUND A monotherapy resulted in tumor stasis. ANTIBODY A alone had marginal growth inhibition. The combination of COMPOUND A and ANTIBODY A led to tumor regression.

The data demonstrate that the combination of COMPOUND A and ANTIBODY A acts synergistically to inhibit PIK3CA mutant breast cancer cells by blocking two interconnected pathways.

Experiment 1—Effect of Combination of COMPOUND a and ANTIBODY a on the Proliferation of Breast Cancer Cell Line MCF7

| Abbreviation | Description |
| --- | --- |
| DMSO | DiMethylSulfOxide |
| E1 | Estrone |
| E2 | 17β-estradiol |
| ER | Estrogen Receptor |
| FBS | Fetal Bovine Serum |
| $IC_{50}$ | 50% Inhibitory Concentration |
| IGF1 | Insulin like growth factor |
| PI3K | Phosphatidyl Inositol 3-Kinase |
| SD | Steroid-Depleted |
| CTG | Cell Titer Glo |
| RTCA | Real Time Cell Proliferation Assay |

Materials and Methods

Preparation of Compounds Solutions

COMPOUND A (10 mM), stored in aliquots at −20° C. ANTIBODY A (0.2 mM in 1% BSA), stored in aliquots at 4° C. Insulin-like Growth Factor-1 (IGF-1; BD BioSciences, #40037) was utilized at 100 ng/mL.

Cell Culture

MCF7 human breast carcinoma cells were stably transfected by a none insert control vector, also named MCF7/3 (1). Unless otherwise mentioned, all MCF7 cell culture reagents were obtained from Invitrogen (Grand Island, N.Y. 14072USA).

MCF7 cells were maintained in minimum essential media (MEM, #11095-080) supplemented with 10% v/v fetal bovine serum (FBS, #10099-141), 1 mM sodium pyruvate (#11360-070), and 1% v/v non-essential amino acids (#11140-050). The cell line was cultured in a humidified incubator at 37° C. in 5% $CO_2$. The cells were passaged twice a week and the medium was changed every 2 to 3 days.

To assess estrogen driven (E2) cell proliferation, it was necessary to deplete the medium of steroids for the MCF7 cell line. This steroid-depleted (SD) medium, MEM (#51200-038, no phenol red and no glutamine) was supplemented with 10% charcoal stripped FBS (#12676-029) and GLUTAMAX (#35050-061). Medium without phenol red (pH indicator) was required, since it is a structural homologue of estrogen. Additionally, normal FBS needed to be replaced by charcoal-stripped FBS in order to remove steroids. TRYPLE EXPRESS (#12604-013, no phenal red) was used for all cell dissociation.

Cell Viability Assay and Cell Proliferation Assay

MCF7 cells were steroid deprived for 2-3 days, trypsinized using TRYPLE EXPRESS and plated (1500 cells/well) on clear-bottom 384-well black plates (Greiner) in triplicate (30 μL/well SD media). Cells were allowed to attach overnight followed by 120 hours (MCF7) of incubation with various concentrations of inhibitor agents or agent combinations (10 μL/well) in the presence or absence of IGF-1.

Cell viability was determined by measuring cellular ATP content using the CELLTITER-GLO (CTG) luminescent cell viability assay (Promega). Each single agent and combination treatment of cells was compared to controls, or cells treated with an equivalent volume of medium. An equal volume of the CTG reagents was added to each well at the end of the compound treatment and luminescence was recorded on an ENVISION plate reader (Perkin Elmer). Reduced and enhanced luminescent signal values (responses) were calculated relative to untreated (control) cells.

Method for Calculating the Effect of Combinations

To evaluate the anti-proliferative activity of COMPOUND A with ANTIBODY A in a non-bias way, as well as to identify synergistic effect at all possible concentrations, the studies were conducted with a "dose matrix." This utilized different permutations of serially-diluted single agents: COMPOUND A, and ANTIBODY A. In combination assay, agents were applied simultaneously and were assessed in the presence and absence of IGF-1.

The "dose matrix", COMPOUND A/ANTIBODY A, consisted of the following:

COMPOUND A, which was subjected to a 7 dose 3× serial dilution, with a high dose of 2.6 μM and a low dose of approximately 3.5 nM ANTIBODY A, which was subjected to a 6 dose 3× serial dilution with a high dose of 566 nM and a low dose of approximately 2.3 nM The synergistic interaction (analyzed using Chalice software [CombinatoRx, Cambridge Mass.]) was calculated by comparing the response from a combination to the response of the agent acting alone, against the drug-with-itself dose-additive reference model. Deviations from dose additives can be assessed numerically with a Combination Index (CI), which quantifies the overall strength of combination effect. This calculation (essentially a volume score) is as follows:

$$V_{HSA} = \Sigma_{X,Y} \ln f_x \ln W_Y(I_{data} - I_{HSA})$$

Additionally, CI is calculated between the data and the highest single-agent surface, normalized for single agent dilution factors (Lehar J et al (2009), "Synergistic drug combinations tend to improve therapeutically relevant selectivity", Nature Biotechnology 27: 659-66 (2009).

Data evaluation and graph generation were performed using Microsoft Excel software, and Chalice software.

Results

A cell proliferation assay was performed to investigate the activity of a combination of COMPOUND A and ANTIBODY A on cell proliferation in IGF1 driven MCF7 cells. In order to evaluate the combination effect in a non-biased way and to identify synergistic effects at different concentrations, the study was conducted using a "dose matrix" scheme, where a combination is tested as described in the method above.

The percentage of inhibition over the entire dose grid is shown in FIG. 1. COMPOUND A displayed concentration dependent anti-proliferative activity either in the presence or absence IGF1, the addition of IGF1 appeared to slightly dampen the COMPOUND A's single agent activity. ANTIBODY A is almost totally inactive in the absence of IGF1, even in the presence of IGF1, it displayed only very moderate activities (10-20% inhibition). The combination of the two inhibitors appears to be synergistic in the presence of IGF1, which is evidenced by the difference in synergy scores (3.32 as compared to 0.15) and the isobolograms. When the two inhibitors were used in combination, the inhibition of cell proliferation was also significantly increased in IGF1 conditions, compared to each agent alone. The dose ranges where enhancement of growth inhibition were observed at combinations of 96 nM-2.6 μM COMPOUND A with 21 nM-566 nM ANTIBODY A and as highlighted with red rectangles in FIG. 1. While in the absence of IGF1, no synergy or enhanced growth inhibition was observed.

Data derived from this study demonstrate that this combination of an alpha-isoform specific PI3K inhibitors and IGF1R inhibitor antibody synergistically inhibits the growth of PIK3CA mutant breast cancers in the presence of IGF1 signaling.

In summary, the combination of COMPOUND A and ANTIBODY A represents an approach against PI3KCA mutant breast cancers.

Experiment 2—In Vivo Experiment

MCF-7 cells (purchased from American Type Culture Collection (ATCC)) were tested free of mycoplasma and viral contamination in the IMPACT VIII PCR assay panel (RADIL, MU Research Animal Diagnostic Laboratory, Columbia, Mo.). MCF-7 cells were cultured in EMEM medium (ATCC#30-2003) containing 10% heat-inactivated fetal bovine serum. Mice were implanted with 17b-estradiol pellets, 0.18 mg/pellet, 90-day release (Innovative research of America Catalog #NE-121), between the shoulder blades three days before the cell implant.

Dose and Schedule for Study

| Group | Drug | Dose (Free base equivalent) | Schedule/ Route | # of mice/ group (n) |
|---|---|---|---|---|
| 1 | Vehicle 1 (0.5% MC) + Vehicle 2 (PBS) | N/A | qd, po q2w, ip | 12 |
| 2 | COMPOUND A | 30 mg/kg | qd, po | 12 |
| 3 | ANTIBODY A | 12 mg/kg | q2w, ip | 12 |
| 4 | COMPOUND A + ANTIBODY A | 30 mg/kg/ 12 mg/kg | qd, po q2w, ip | 12 |

The following abbreviations are used in the above table:
"qd" - administration once daily,
"q2w" - administration twice each week,
"po" - administration per oral galvage,
"ip" - administration by intraperitoneal route Treatment started on day 21 and concluded by day 59. Tumor volume of each group was measured. The effect of COMPOUND A and ANTIBODY A, as monotherapy and combination, was assessed by comparing:

(a) the percent change between Day 1 and endpoint day in the mean tumor volume of the treated group (T) and the control group (C) (herein referred to as "T/C"), and (b) the percent change between Day 1 and the endpoint day in the mean tumor volume of the treated group compared to its initial volume (herein referred to as "$T/T_0$").

Figure 2:
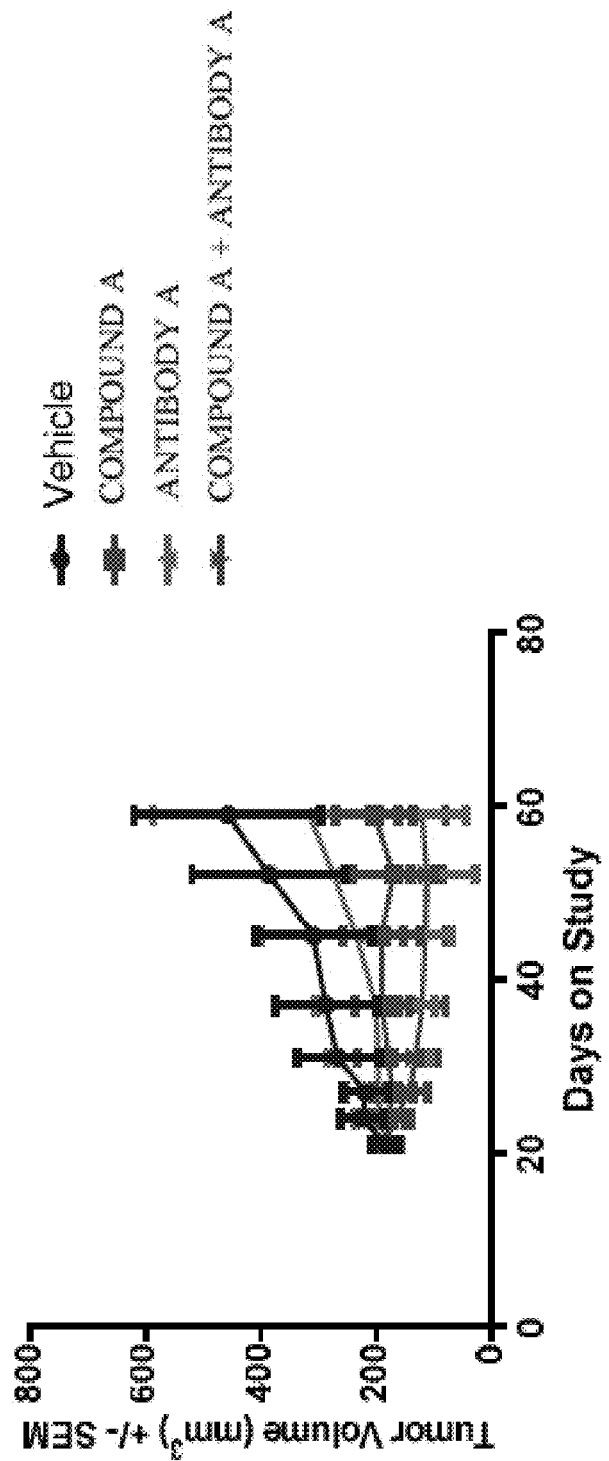
FIG. 2 is a graph showing the effects of COMPOUND A, ANTIBODY A, and the combination of COMPOUND A and ANTIBODY A on tumor volume in mice.

Following this procedure, COMPOUND A monotherapy yielded T/C of 10% (p<0.05, compared to vehicle). ANTIBODY A yielded T/C of 48% (not statistically significant, compared to vehicle). The combination of COMPOUND A and ANTIBODY A achieved tumor regression $T/T_0$ of −35% (p<0.0001, compared to vehicle). The results are shown in FIG. 2.

We claim:

1. A method for treating cancer in a subject in need thereof comprising administering to the subject a therapeutically effective amount of:
   a) the alpha-isoform specific phosphatidylinositol 3-kinase (PI3K) inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (COMPOUND A) or a pharmaceutically acceptable salt thereof; and
   b) an insulin-like growth factor-1 receptor (IGF1R) inhibitor which is an antibody comprising a heavy chain and a light chain, wherein the heavy chain comprises a variable region comprising the complementarity determining region (CDR) amino acid sequences set forth in SEQ ID NOs: 5, 6, and 7, and wherein the light chain comprises a variable region comprising the CDR amino acid sequences set forth in SEQ ID NOs: 8, 9, and 10; and wherein the cancer is ovarian cancer or breast cancer.

2. The method of claim 1, wherein the antibody comprises a heavy chain variable region comprising the amino acid sequence of SEQ ID NO: 3, and a light chain variable region comprising the amino acid sequence of SEQ ID NO: 4.

3. The method of claim 2, wherein the antibody comprises a heavy chain comprising the amino acid sequence of SEQ ID NO: 1, and a light chain comprising the amino acid sequence of SEQ ID NO: 2 (ANTIBODY A).

4. The method of claim 1, wherein the PI3K inhibitor and the IGF1R inhibitor are in a single formulation or unit dosage form.

5. The method of claim 1, wherein the PI3K inhibitor and the IGF1R inhibitor are in separate formulations or unit dosage forms.

6. The method of claim 5, wherein the PI3K inhibitor is administered orally, and the IGF1R inhibitor is administered intravenously.

7. The method of claim 1, wherein the PI3K inhibitor and/or IGF1R inhibitor are administered at substantially the same time.

8. The method of claim 1, wherein the PI3K inhibitor and/or IGF1R inhibitor are administered at different times.

9. The method of claim 8, wherein the PI3K inhibitor is administered orally, and the IGF1R inhibitor is administered intravenously.

10. The method of claim 1, wherein the cancer is resistant or refractory to treatment with an epidermal growth factor receptor (EGFR) inhibitor or IGF1R inhibitor.

11. The method of claim 1, wherein COMPOUND A is administered at a dosage range from about 0.05 to about 50 mg per kilogram body weight of the recipient per day.

12. The method of claim 1, wherein ANTIBODY A the IGF1R inhibitor is administered at a dosage of between about 9 and 20 mg/kg.

13. The method of claim 1, wherein the cancer is a breast cancer that is amplified hormone receptor positive or has a mutated PIK3CA gene.

14. The method of claim 1, wherein the cancer is an ovarian cancer that has a PIK3 CA gene mutation or amplification.

15. A method for treating an ovarian cancer or a breast cancer that is resistant or refractive to treatment with the IGF1R inhibitor ANTIBODY A comprising administering a therapeutically effective amount of the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to a subject in need thereof.

16. A method for treating an ovarian cancer or a breast cancer that is resistant or refractive to treatment with the PI3K inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof comprising administering a therapeutically effective amount of the IGF1R inhibitor ANTIBODY A.

* * * * *